United States Patent
Düsterhöft et al.

(10) Patent No.: US 6,451,260 B1
(45) Date of Patent: Sep. 17, 2002

(54) METHOD FOR PRODUCING MICROPOROUS ELEMENTS, THE MICROPOROUS ELEMENTS THUS PRODUCED AND USES THEREOF

(75) Inventors: Andreas Düsterhöft, Hilden; Thomas Manz, Düsseldorf; Ehrenfried Mehl, München; Friedrich Lottspeich, Stockdorf, all of (DE)

(73) Assignee: Dyax Corp., Cambridge, MA (US)

( * ) Notice: Subject to any disclaimer, the term of this patent is extended or adjusted under 35 U.S.C. 154(b) by 0 days.

(21) Appl. No.: 09/242,786
(22) PCT Filed: Aug. 26, 1997
(86) PCT No.: PCT/EP97/04653
§ 371 (c)(1), (2), (4) Date: Mar. 9, 1999
(87) PCT Pub. No.: WO98/08594
PCT Pub. Date: Mar. 5, 1998

(51) Int. Cl.[7] .................. G01N 15/06; G01N 33/00; G01N 33/48; B27N 3/08; B27N 3/10
(52) U.S. Cl. .............. 422/68.1; 422/100; 422/283; 264/239; 264/257
(58) Field of Search ................ 422/68.1, 100, 422/283; 264/239, 257

(56) References Cited

U.S. PATENT DOCUMENTS

| | | | |
|---|---|---|---|
| 3,591,010 A | * 7/1971 | Pall | 210/493 |
| 3,865,548 A | 2/1975 | Padawer | 23/230 R |
| 4,540,625 A | 9/1985 | Sherwood | 428/283 |
| 5,156,811 A | 10/1992 | White | 422/150 |

FOREIGN PATENT DOCUMENTS

| | | | |
|---|---|---|---|
| DE | 39 27 787 A1 | 2/1991 | B01D/61/36 |
| DE | 39 39 867 A1 | 6/1991 | B01D/71/82 |
| EP | 0 118 735 | 9/1984 | B01L/3/00 |
| EP | 0 312 394 | 4/1989 | G01N/33/53 |
| EP | 0 413 552 A1 | 2/1991 | B01D/71/56 |
| EP | 0 505 118 A2 | 9/1992 | B01L/3/02 |
| EP | 0 532 282 A1 | 3/1993 | B01D/71/02 |
| EP | 0 588 564 A1 | 3/1994 | B01D/15/00 |
| WO | WO 87/01956 | 4/1987 | B01D/23/28 |

OTHER PUBLICATIONS

Ullmann's Encyclopedia of Industrial Chemistry, vol. A16, 5th ed., VCH Verlagsgesellschaft mbH, D–6940 Weinheim (Federal Republic of Germany) (1990).

Kirk–Othmer: Encyclopedia of Chemical Technology, vol. 15, 3rd edition, John Wiley & Sons, NY (1981).

* cited by examiner

Primary Examiner—Jezia Riley
(74) Attorney, Agent, or Firm—Leon R. Yankwich; David G. O'Brien

(57) ABSTRACT

Described are novel methods for producing microporous elements and microporous elements obtainable by such methods. Provided are also microporous elements including solid microparticles, which preferably modify the adsorptive properties of the microporous element. Described are also microporous elements which are linked to a support and/or a retainer as well as methods for their production. Filter elements comprising the above-described microporous elements are also provided. Furthermore, kits, diagnostic and pharmaceutical compositions comprising the aforementioned microporous or filter elements are described. Furthermore, uses of the aforementioned microporous and filter elements in microfiltration, chromatography, adsorption/immobilization of organic and inorganic compounds as well as for the preparation and/or detection of such compounds are disclosed.

31 Claims, 4 Drawing Sheets

METHOD FOR PRODUCING MICROPOROUS ELEMENTS, THE MICROPOROUS ELEMENTS THUS PRODUCED AND USES THEREOF

The present invention relates to novel methods for producing microporous elements and microporous elements obtainable by such methods. The present invention also provides microporous elements comprising solid microparticles, which preferably modify the adsorptive properties of the microporous element. Described are also microporous elements which are linked to a support and/or a retainer as well as methods for their production. The present invention also relates to filter elements comprising the above-described microporous elements. Furthermore, the present invention relates to kits, diagnostic and pharmaceutical compositions comprising the aforementioned microporous or filter elements. Furthermore, the present invention relates to the use of the aforementioned microporous and filter elements in microfiltration, chromatography, adsorption/immobilization of organic and inorganic compounds as well as for the preparation and/or detection of such compounds.

There is an increasing demand in the area of analytical chemistry for devices capable of handling moderate to small sample volumes, in a manner which is rapid, gives high recovery and minimizes any possibility of sample contamination. Among other desired attributes are low cost, ease of manufacture and suitability for application with conventional equipment. Previous devices for micro filtration etc. involve the use of preformed filter material. Synthetic polymers such as nylon, methacrylate or semisynthetic polymers such as nitro cellulose, or cellulose acetate have been used over decades. Mostly the filter material is a nonwoven material which is formed from a web of synthetic or natural fibers. The fibers may or may not be bonded together by a binder. In general, discs are cut from the nonwoven material and positioned within a sample tube or the like. Problems in connection with this previous approach include an insufficient contact of the pre-cut filter disc to the wall of the filter tube leaving small gaps and thereby allowing the applied liquid sample to escape. In this context, the filter disc may be attached to the filter tube by an adhesive; additionally or alternatively, the filter disc may be welded into the filter tube by locally applying heat or by ultrasonic treatment. If the filter disc is attached to the filter tube by an adhesive, the adhesive may influence the filter properties of the material in an uncontrollable manner. The same holds true when the filter disc is welded into the filter tube by locally applying heat or by ultrasonic treatment. The problems discussed above are enhanced when the overall size of the filter element is reduced. It has therefore hitherto not been technically feasible to produce satisfactory filter elements with apertures of a diameter as low as several micrometer. When using an adsorptive filter containing granular adsorptive microparticles, the problem of dislocation might occur during processing of a liquid and also during transportation. Therefore, the microparticles are held for example in between two confining porous elements, such as frits, nets, annular or grooved retainers at both porous sides of the filter element. Even when embedded between fibers of teflon or glass, an upper porous retainer as well as a lower supporting frit, net or grooved element might be necessary.

Thus, the technical problem underlying the present invention is to provide a cost-effective method for producing a microporous element, which can be applied for most versions of analytical or micro preparative liquid chromatography such as ion exchange chromatography, reverse phase chromatography, hydrophobic interaction chromatography, adsorption chromatography at silica gels, affinity chromatography, immuno chromatography, for binding studies, the isolation of multi component binding complexes, for the screening of samples or for preventing the dislocation of microparticles, improved or simplified by applying selected suitable techniques, avoiding unspecific loss of biopolymers like peptides, proteins, nucleic acids, oligonucleotides, polysaccharides or derivatives thereof by presenting biocompatible surfaces, and saving cost by using expensive microparticle material in very small amounts. In addition transfer of separated substances from the filter to blotting membranes shall be rendered possible without having problems with dead volumes. The solution to the technical problem is achieved by providing the embodiments characterized in the claims.

Accordingly, the present invention relates to a method for producing a microporous element, comprising the steps of
 a) applying a substance; and
 b) causing solidification in spongy form of at least part of the substance.

In context with the present invention, the term "solidification in spongy form" means that the product contains void spaces.

In a preferred embodiment the method of the present invention the substance is present in a liquid phase. Said liquid phase may be preferably a solution or suspension of a polymer in a solvent and the solidification in spongy form is preferably caused by the action of a non-solvent for the polymer.

For a purpose of the present invention, the term "polymer" means natural or artificial substances made up of large molecules which are themselves made from combinations of small simple molecules which are identical or not, i.e. homo- and co-polymers. Polymers according to the present invention include also resins.

In a preferred embodiment the polymer is selected from the group consisting of polyvinyl esters, partially deacylated polyvinyl esters, cellulose derivatives, polyamides, polystyrene, poly(methyl methacrylate) and mixtures thereof. Preferably, said polymer comprises both hydrophilic and hydrophobic segments within its molecules.

In a particularly preferred embodiment the method of the present invention, the polymer is selected from the group consisting of poly(vinyl alcohol-co-ethylene), poly(vinyl alcohol-co-vinylacetate), ethylene acrylic acid copolymer, ethylene acrylic ester copolymer, ethylene acrylamide copolymer, acrylic acid vinylacetate copolymer, acrylamide vinylacetate copolymer, copolymer of acrylic acid ethylene diamine monoamide with vinylacetate, poly(vinyl alcoholco-styrene), poly(styrene-co-maleic acid) and glycerol ester derivatives thereof, acrylamide acrylic ester copolymer, and mixtures thereof.

In another preferred embodiment the method of the present invention the solvent is selected from the group consisting of dimethyl sulfoxide, dimethylformamide, dimethylacetamide, formamide, formic acid, acetic acid, 2,2,2-trichloro ethanol, toluene, tetrahydrofuran and mixtures thereof.

In a further preferred embodiment the solvent is comprised of at least two volatile non-solvents. Preferably, said solvent is removable at ambient temperatures or vacuum.

In a further preferred embodiment of the method of the present invention the solidification is achieved by evaporating the solvent and/or non-solvent. Preferably, the nonsolvent is selected from the group consisting of water, alcohols having 1 to 4 carbon atoms, ammonia, ethylacetate, acetone, ethylene diamine, and mixtures thereof.

In another embodiment of the method according to the present invention the liquid phase is a hydrocolloid.

In a preferred embodiment the hydrocolloid is selected from the group consisting of low melting agarose, starch, polyvinyl alcohol, and mixtures thereof.

In a further preferred embodiment the layer of hydrocolloid solution is subjected to crosslinking by sodium tetraborate.

In another preferred embodiment the solidified hydrocolloid is desiccated and/or crosslinked.

In another embodiment of the method according to the present invention the liquid phase is a solution or suspension of one or more monomer(s) and the solidification is caused by polymerizing said monomer.

In a preferred embodiment the monomer(s) is (are) present in a solvent. Preferably, the monomer(s) comprise(s) one or more crosslinking monomers.

In a particularly preferred embodiment said monomers comprise a diamine and a diepoxide.

In a further preferred embodiment of the method according to the present invention, the monomer is selected from the group consisting of vinylesters, acrylic acid and its derivatives, and polymerization is effected under the influence of free radicals.

In a further embodiment of the method according to the present invention the substance is permeated with a channel-sparing fluid or with reversible hydrogel or with liquids such as polypropylenglykol of 4000 Dalton or higher being insoluble in water at temperatures above 20°. Preferably, the channel-sparing fluid is silicon oil, water or air.

In another embodiment of the method according to the present invention the substance is thermoplastic polymer and the solidification is caused by sintering, e.g. by heating or the action of a solvent. Preferably, the polymer is a styrene-maleic acid copolymer or polyvinylacetate.

In a further embodiment of the method according to the present invention the substance further comprises solid microparticles, preferably having a size from 0.01 μm to 500 μm. Regarding size, porosity and adsorbent characteristics, one microporous element may be made up of different types of microparticle which may be immobilized in a layered order. The microparticles such as adsorbent particles are commercially available. Some are made of inorganic material like calcium phosphate, silica gel or oxides of silicon, aluminum, titan, zirconium or, consist of an microporous inorganic core with a surface layer of organic polymer, providing anionic and cationic groups for ion exchange chromatography or hydrophobic groups for reversed phase- and hydrophobic interaction chromatography. The microparticles may be also derivatized such that they meet the requirements of specific binding of affinity chromatography of proteins, polypeptides, nucleic acids, oligonucleotides, polysaccharides and other organic substances. By covalent binding, or by non-covalent binding such as tag-binding, these substances themselves may be used to form an affinity matrix, in addition to, e.g., antibodies, avidin and lectins.

In a preferred embodiment the substance and the microparticles are present as a suspension in a non-solvent of low viscosity.

Said substance and said microparticles can be solidified, for example by evaporating from a very diluted solution in a poor solvent or, by sintering at moderate temperatures up to 130° C. without polymer solution, using only partially molten polymer instead.

In a preferred embodiment of the above-described method of the invention said microparticles modify the adsorptive properties of the final microporous element, preferably useful for ion exchange chromatography, reverse phase chromatography, hydrophobic interaction chromatography, adsorption chromatography at silica gels and/or affinity chromatography.

In a further embodiment of the method of the present invention the microparticles are designed to have a preselected property. Thus, the microparticles may contain, e.g. an effector molecule. Examples of such a molecule include amino acid sequences designed to sequester ions, which makes the molecule suitable for use as an imaging agent, and sequences designed to facilitate immobilization of the microparticles for use, e.g., in affinity chromatography and solid phase immunoassay. Another example of such a molecule is a bioactive effector molecule, that is a protein having a conformation suitable for biological and/or enzymatic activity, such as an enzyme, toxin, receptor, binding site, growth factor, cell differentiation factor, cytokinin, hormone, or anti-metabolite.

In a preferred embodiment said microparticles comprise an effector molecule capable of sequestering an ion, selectively binding to a solid support, binding to a preselected antigenic determinant or being a ligand. For example, said molecule may comprise an enzyme or remotely detectable moiety and/or a sequence of amino acids, nucleic acids or analogs or derivatives thereof.

Preferably, said molecule capable of sequestering an ion is calmodulin, metallothionein, a fragment thereof, or an amino acid sequence rich in at least one of glutamic acid, aspartic acid, lysine and arginine and said effector molecule capable of binding to a preselected antigenic determinant is an antibody or fragment or a derivative thereof. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to antigens can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the desired antigen as well as for the monitoring of the presence of such antigens, for example, in recombinant organisms, and for the identification of compounds interacting with the antigen. For example, surface plasmon resonance as employed in the BIAcore system may be combined with a microporous element of the invention to increase the efficiency of phage antibody selections, yielding a high increment of affinity from a single library of phage antibodies which bind to an epitope of the antigen (Schier, Human Antibodies Hybridomas 7 (1996), 97–105; Malmborg, J. Immunol. Methods 183 (1995), 7–13).

Furthermore, said molecule capable of selective binding to a solid support can be, e.g., GST, His-tag, Lex-A, MBP and said ligand, e.g., Ni—NTA.

In a still further embodiment of the method of the present invention the substance is self-sustaining and applied to a support.

A "support" in accordance with the present invention, can be, for example, in the form of an aperture suitable for applying the substance so as to form a preferably self-sustaining layer over the cross section of the aperture.

Preferably, the support is formed of polypropylene (PP), polyethylene (PE), propylene/ethylene copolymer, polyvinyl acetate, polyamide, polystyrene, polyethylene terephthalate (PET), polyether etherketon (PEEK), polycarbonate, polyethylene vinylacetate, poly(vinyl alcohol-co-ethylene), polyester, polyamide, glass, ceramics, quartz, silicon nitride, or mixtures thereof, or composite materials thereof with fibers or frames of glass, silicon dioxide, carbon or ceramics.

In a preferred embodiment the support has the form of a tube, and the microporous element is generated at or near to one edge of the tube. Preferably, at least a section of the tube is of conical form, having a smaller and a larger cross-section end, and the microporous element is generated at or near to the smaller cross-section end.

In a preferred embodiment of the method according to the present invention the step of applying the solution to the aperture is accomplished by allowing the solution to ascend in the tube by capillary action.

The inner wall of the tube may be coated with a hydrophilic coating while the edge of the tube next to the microporous element may be kept free of hydrophilic coating or not. Preferably, the coating is formed by applying a solution of one or more polyvinyl esters in an organic solvent to the inner wall of the tube, allowing the organic solvent to evaporate, and partially hydrolyzing the resulting layer of polyvinyl ester at the surface thereof.

The diameter of the aperture of the support can be from 0.02 mm to 4 mm.

In an alternative embodiment of the method according to the present invention the substance is applied to a retainer.

Preferably the retainer is microporous and/or the solid particles are connected with each other.

In a preferred embodiment the microporous retainer is formed of polyethylene (PE), polypropylene (PP), propylene/ethylene copolymer, polyvinyl acetate, polyamide, polystyrene, polyethylene terephthalate (PET), polyether etherketon (PEEK), polycarbonate, poly(vinyl alcohol-co-ethylene), polyester, polyamide, glass, ceramics, quartz, silicon, silicon nitride, or mixtures thereof, stainless steel, or composite materials thereof with fibers or frames of glass, silicon dioxide, carbon or ceramics.

Said microporous retainer is preferably in the form of a disc, grid, large-pore membrane, membrane with supporting fabric, membrane with woven or unwoven characteristics, net, plate, rod and/or truncated cone.

Advantageously, the microporous element is generated within the support.

In a preferred embodiment of the methods described above the support is hollow moisture-impervious.

In a preferred embodiment the method according to the present invention further comprises the step of arranging at least one microporous membrane at the microporous retainer. Preferably, the microporous membrane is formed of (regenerated) cellulose, polyamide, polyester, polypropylene (PP) or polytetrafluorethylene (PTFE, Teflon®).

In another preferred embodiment of the method according to the present invention said retainer and/or said support is removed after solidification.

Furthermore, the present invention relates to a microporous element obtainable according to a method of the invention as described above. Preferably, the microporous element according to the present invention is in the form of a disc, grid, membrane with supporting fabric, membrane with woven or unwoven characteristics, net, plate, rod or truncated cone.

The present invention also relates to a filter element comprising the microporous element of the invention or obtainable according to the present invention.

Preferably, the polymer is attached to at least one part of the outer surface of the microporous retainer in the filter element according to the present invention. Advantageously, the microporous retainer in the filter element according to the present invention contains in its pores the polymer in such a manner that the pores have residual free spaces forming channels allowing the flow of a fluid through the filter element.

In a particularly preferred embodiment the filter element according to the present invention the average diameter of the microparticles is less than 50% of the average diameter of the pores.

Another embodiment of the present invention relates to a multiple channel filter element, comprising a plurality of filter elements according to the present invention. This embodiment is particularly suitable for high throughput screening of samples and can be employed, for example, for forensic analysis, high throughput nucleic acid preparation, sample preparation for diagnostic application or drug screening application, which usually requires the analysis of many samples.

In still another embodiment the present invention relates to a kit comprising a microporous element of a filter element described above. The kit according to the present invention may further contain compounds and/or devices which are suitable, for example, for the preparation or purification of biomolecules like proteins, peptides, nucleic acids, oligonucleotides, polysaccharides or derivatives thereof. Also, for example, devices such as syringes or hollow needles may be comprised in the kit of the invention.

Moreover, the present invention relates to a diagnostic composition comprising a microporous element or a filter element of the present invention. For example, in the preparation of analytical devices which are suitable for the use in home, clinic or doctor surgery and which are intended to give an analytical result which is rapid and which requires a suitable permeable material. The principle of such devices is described, for example, in EP-A-0 291 194, EP-A-0 225 054, EP-A-0 183 442 and EP-A-0 186 799. Moreover, microporous and filter elements of the present invention can be used for the high throughput screening of combinatorial nucleic acid or peptide libraries.

Also, the present invention relates to a pharmaceutical composition comprising a microporous element or a filter element described above. For example, the microporous and filter elements of the invention can be used for the dosed release of the active ingredients of the pharmaceutical composition.

The present invention also provides for the use of a microporous element or a filter element described herewith for any kind of micro filtration, solid-liquid separation, clearing of solutions, harvesting of pro- and eukaryotic cells, removal and purification of cellular fragments and debris, immobilization of fragments, viruses and plasmids, adsorption/immobilization of proteins, polypeptides, nucleic acids, oligonucleotides or as retainer for granular material, as used in affinity chromatography, immuno chromatography, for binding studies, the isolation of multi component binding complexes, for the screening of samples, or for preventing the dislocation of microparticles. Furthermore, the microporous and filter elements of the invention can be used, for example, as filter elements to reduce the emission and/or presence of undesired substances such as odorous and toxic substances. For this purpose, the microporous and filter elements of the invention comprise suitable adsorptive substances such as charcoal contained, for example, in the microparticles. Furthermore, the microporous and filter elements of the invention can be used in the preparation of starch graft polymers. These products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. In the last few years, these super absorbers have been used mainly in the hygiene field, e.g. in products such as diapers and sheets, as well as in the agricultural sector, e.g. in seed pellets.

In a particularly preferred embodiment of the use of the invention the microporous or filter element is used for the preparation and/or detection of compounds comprising nucleic acids, proteins, organic compounds, or derivatives or analogs thereof such as peptidomimetics or PNA. Said compound can be derived from natural or non-natural sources. Natural sources comprise organisms, i.e. cell and tissues of such organism as well as samples derived from the natural environment. Non-natural sources include enzymatic products generated in vitro and chemically synthesized. It is directly evident for the person skilled in the art that the microporous and filter elements of the present invention are suitable for the isolation, purification and/or detection of any desired compound derived, e.g. from a cell including DNA, RNA, protein and other cell components. Furthermore, it is possible to isolate and identify aggregates and complexes of such compounds. Besides, the isolation and purification of such compounds from natural sources, e.g. from samples of a cell, body fluids, air, water and soil, it is envisaged to employ the microporous and filter elements of the invention for the purification of synthetically produced compounds.

Further use of the microporous and filter elements of the present invention comprise the in use in assays or detection of specific binding partners. For this purpose, at least one agent supposed to be capable of binding to at least one binding partner is comprised in the microporous element of the invention or for example linked with the microparticles. The microporous element either alone or in any of the above described embodiments then is contacted with a sample suspected to contain at least one binding partner for the agent. Specific binding partners may then be released from the microporous element and detected by methods known to those skilled in the art. Thus, the microporous and filter elements of the present invention can be used for the isolation and/or detection of, e.g. receptors bound to their ligands and for the preparation of so-called "ligand traps". Furthermore, once, a complex or for example a receptor ligand complex is trapped in the microporous element of the present invention, a further sample of compounds can be contacted with said microporous element in order to identify compounds which interfere with the binding of said receptor and its ligand. Said compound can then be used as antagonist or agonist of one of the binding partners depending on the action of said compound exhibited in vivo. Furthermore, the microporous and filter elements of the present invention can be used for pharmaceutical screening for ligands of low molecular weight in ultrafiltrates that are capable of forming specific complexes with nucleic acids or proteins like recombinant receptor proteins applying, preferably, the multicolumn multichannel filter plate of the invention for removal of free ligands and for blotting-transfer of the complexed ligand to an attached membrane matrix or target plate for further analysis by known analytical techniques such as mass-spectrometry including the MALDI technique. Since assays using the microporous and filter elements of the present invention can be performed at low cost and high throughput, it is furthermore expected that the microporous and filter elements of the present invention can substitute devices such as gel electrophoresis of nucleic acids and proteins or systems for the detection of specific binding partners such as the two-hybrid-system.

Thus, microporous and filter elements of the present invention can also be used with for the high throughput screening of combinatorial nucleic acid or peptide libraries or, for example, for the use of solid phase PCR.

The method for producing a microporous and/or filter element according to the present invention may be performed in combination of any one of the embodiments described above. For example, by generating a microporous element within an aperture of a solid moisture-impervious support, comprising the steps of applying a liquid phase to the aperture so as to form a self-sustaining liquid layer over the cross-section of the aperture; and causing solidification in spongy form of at least part of the liquid phase. Accordingly, the microporous element is generated in situ from a liquid precursor. The liquid precursor readily takes a shape that matches the shape of the aperture in the support. Any imperfections like burrs etc. of the aperture are hereby compensated for. Upon solidification, a microporous element is obtained, which snugly fits into the aperture of the support and has complete circumferential contact to the walls thereof.

Preferably, the support is formed of a plastic such as polypropylene, polyethylene, propylene/ethylene copolymer, polyvinyl acetate, polyamide, polystyrene, polyethylene terephthalate, polyether etherketon (PEEK), polycarbonate, polyethylene vinylacetate, polyester, polyimide, or mixtures thereof. Also included are composite materials of plastic with fibers or frames of glass, silicon dioxide, carbon or ceramics.

Usually, the support has the form of a tube, preferably with circular cross-section, and the microporous element is generated at or near to one edge of the tube. In order to facilitate sample application and for accommodation of greater sample volumes, preferably at least a section of the tube is of conical form, having a smaller and a larger cross-sectional end, with the microporous element generated at or near the smaller cross-sectional end. For example, the support is a pipette tip such as commonly used with Eppendorf pipettes. In order to prevent dislocation, such as slipping, of the microporous element formed, the tube may have a structured inner surface, like a surface with rings or grooves.

It is also envisaged to arrange a plurality of supports, e.g., up to several hundreds, in parallel alignment to form a multiple channel filter element. The multiple channel filter element will allow a biological sample to be tested simultaneously against hundreds of reagents. Alternatively, the support can comprise a plurality of apertures, e.g., in the form of parallel bores or tapered holes. When the multiple channel element is to be evaluated optically, it is convenient to include an opacifying agent such as carbon black into the support material to prevent interference from neighboring channels.

There are several possibilities of applying the liquid phase to the aperture of the support. The various methods will be exemplified with reference to a tubular support but will not be limited thereto. As the liquid phase in general is a solution the terms "liquid phase" and "solution" will be used interchangeably unless otherwise required by the context. Conveniently, application of the solution to the aperture is accomplished by allowing the solution to ascend in the tube by capillary action. The support, for example a tube, is dipped into the solution and raised again. Due to the surface tension of the solution, a liquid layer will remain in the aperture over the cross-section of the aperture. If, for example, the viscosity of the solution is too high different methods for applying the solution to the aperture may be adopted. The ascending force of the solution may be enhanced by temporarily sealing the distant end of the tube, slightly heating the tube, then dipping the tube with its free end into the solution, and allowing the tube to cool to ambient temperature, whereby the solution is drawn into the tube by the volume contraction of the enclosed air. Alternatively, the solution can be introduced from the distant end of the tube and may be brought into its final position by centrifugation. Preferably, the end at or near to which the microporous element is to be formed is sealed with a cap or by pressing against an elastic plate. The cap or the elastic plate preferably has microgrooves or micropores for allowing the enclosed air to escape. Then the arrangement is subjected to centrifugation during which the solution migrates to the end of the tube where it is retained at least partially by the cap or elastic plate. The cap or the elastic plate may be removed before or after solidification, in particular before solidification of the solution or of a part of the solution.

The practitioner often faces the problem that aqueous samples that are introduced in containers made of hydrophobic material tend to adhere to the wall in drops rather than flowing down and collecting at the bottom. In order to avoid this phenomena, the inner wall of a tube which acts as support for a filter element according to the invention, may be coated with a hydrophilic coating. The hydrophilic coating will prevent aqueous samples from adhering to the wall of the support tube. Also, there is no adsorptive loss of biopolymers due to adsorption to the wall of the support. If the inner wall of the tube is coated with the hydrophilic coating, the edge of the tube next to the microporous element is preferably kept free of hydrophilic coating. This will prevent sample liquids which exit from the edge of the tube next to the microporous element from creeping to adjacent filter elements, especially in the embodiment of the present invention where a plurality of filter elements is arranged to form a multiple channel filter element.

The hydrophilic coating is conveniently prepared by applying a solution of one or more polyvinyl esters in an organic solvent to the inner wall of the tube, allowing the organic solvent to evaporate, and optionally partially hydrolyzing the resulting layer of polyvinyl ester at the surface thereof. Suitable polyvinyl esters include polyvinyl acetate (a molecular weight of about 500000 is generally suitable), polyvinyl propionate and polyvinyl stearate.

Partial hydrolysis of the layer of polyvinyl ester is performed by contacting the layer of polyvinyl ester with an alkaline aqueous solution, such as sodium hydroxide. The edge of the tube next to the microporous element can be kept free of hydrophilic coating by applying the solution of polyvinyl ester only to a part of the inner wall of the tube, for example by partially immersing the tube into the solution of polyvinyl ester. After hydrolysis, the microporous element can be generated at or near to the edge of the tube, that has not been brought into contact with the polyvinyl ester solution. Alternatively, the entire inner wall of the tube can be coated with polyvinyl ester, but only part thereof is hydrolyzed.

Alternatively, the hydrophilic coating can be generated by using a high molecular weight polypropylene glycol, for example having a molecular weight of 4000 or higher. Such polypropylene glycols show moderate to good solubility in cold water, however poor solubility in warm water. Accordingly, a cold aqueous solution of polypropylene glycol, for example at 0° to 4° C., might be introduced into the tube and subsequently the temperature is raised, for example to about 20° C. The polypropylene glycol coming out of the solution shows a high affinity to the inner wall of the tube and deposits thereon as a thin layer. Excess polypropylene glycol solution is then removed. Additional chemical crosslinking may be advantageous in some cases.

Employing the method(s) according to the present invention, filter elements having an aperture of a diameter from 0.02 mm to 4 mm, in particular from 0.2 to 2.0 mm, can be produced.

The method of the present invention for producing a filter element by generating a microporous element can be performed, e.g. within an aperture of a solid moisture-impervious support, comprising the steps of providing a solution of a synthetic or semi-synthetic polymer (resin) in a solvent; applying the solution to the aperture so as to form a self-sustaining liquid layer over the cross-section of the aperture; and causing a nonsolvent to diffuse into the layer, which nonsolvent is miscible with the solvent, whereby the resin precipitates to form the microporous element.

Preferably the resin is selected from the group consisting of polyvinyl esters, partially deacylated polyvinyl esters, cellulose derivatives, polyamides, and mixtures thereof. Among polyvinyl esters polyvinyl acetate, polyvinyl propionate, polyvinyl stearate, and polyvinyl cinnamic acid ester; among cellulose derivatives nitrocellulose, and cellulose propionate are to be mentioned. A suitable polyamide is Nylon 6/6.

In certain instances, the resin preferably comprises both hydrophilic and hydrophobic segments within its molecules. Suitable resins include poly(vinyl alcohol-co-ethylene), poly(vinyl alcohol-co-vinylacetate), ethylene acrylic acid copolymer, ethylene acrylic ester copolymer, ethylene acrylamide copolymer, acrylic acid vinylacetate copolymer, acrylamide vinylacetate copolymer, copolymer of acrylic acid diamine monoamide with vinylacetate, poly(vinyl alcohol-co-styrene), acrylamide acrylic ester copolymer, and mixtures thereof. Specifically, copolymers of acrylamide with hexyl acrylate, propyl acrylate or dodecyl acrylate are useful.

Preferably the solvent is selected from dimethyl sulfoxide, dimethylformamide, dimethylacetamide, formamide, formic acid, acetic acid, 2,2,2-trichloro ethanol, and mixtures thereof.

Preferably the nonsolvent is selected from water, alcohols having 1 to 4 carbon atoms, ammonia, ethylacetate, acetone, ethylenediamine, and mixtures thereof. The nonsolvent may be either liquid or gaseous.

The nonsolvent is caused to diffuse into the liquid layer of the resin solution by various methods. A liquid nonsolvent may be brought into contact with the liquid layer of resin solution from one or both sides thereof, for example by dipping the end of the tube at which the layer of resin solution is positioned into a liquid nonsolvent. Additionally or alternatively, the nonsolvent may be introduced from the distant end of the tube. If a gaseous nonsolvent is to be used, the arrangement of support with layer of resin solution is positioned within an atmosphere which is saturated or nearly saturated with the vapors of the nonsolvent. Precipitation may also be accomplished in two successive steps by firstly applying gaseous nonsolvent and, after partial solidification, subsequently applying liquid nonsolvent.

Plane upper and lower surfaces of the microporous element are obtained when the final concentration of nonsolvent in the resin solution during precipitation is raised to about 50% by weight. A plane upper surface allows for a more uniform filtration performance of the filter element. A plane lower surface provides even contact with, e.g., blotting membranes onto which an adsorbed material is to be transferred.

Typical combinations of resin/solvent/nonsolvent are, for example, one of poly(vinylalcohol-co-ethylene), nitrocellulose, cellulose propionate, or polyvinylacetate as resin, dimethyl sulfoxide as solvent and water as nonsolvent; or polyamides (like Nylon 6,6) as resin, 2,2,2-trichloro ethanol as solvent and acetone as nonsolvent.

Without intending to be bound to theory it is believed that in generating the microporous element according to the present invention the following mechanisms are involved: When the nonsolvent diffuses into the layer of resin solution, the solubility of the resin is gradually decreased. As the limit of solubility is reached the resin begins to precipitate from the solution at individual points. The precipitation of the resin proceeds at the points of initial precipitation. Ultimately, the solvent/nonsolvent is enclosed in large interconnecting enclaves in a solid matrix of resin. The interconnecting enclaves form the liquid-permeable channels of the final microporous element. If a synthetic resin is used which comprises both hydrophilic and hydrophobic segments, the hydrophobic segments will be forced towards each other and brought into contact with each other as the concentration of nonsolvent in the resin solution increases. There will be interactions between the hydrophobic segments of neighboring molecule chains, which result in the formation of a crystalline hydrophobic backbone of the precipitated resin. The hydrophilic segments will be oriented towards the enclaves filled with solvent/nonsolvent. Accordingly, a microporous element is obtained where the liquid-permeable channels are predominantly hydrophilic. This provides the benefit of biocompatibility. The term "biocompatibility" means that the three-dimensional structure of biopolymers, for example proteins, peptides, nucleic acids, oligonucleotides, polysaccharides or derivatives thereof, is maintained. The interphase forces are less destructive when the polymer surface is rich in hydroxyl, amide or ether groups.

In order to modify the adsorptive properties of the microporous element, the solution of the synthetic resin may further comprise solid microparticles. The micro particles may be composed of silicon dioxide, silica gel, aluminum oxide, titan dioxide, zirconium oxide, glass, carbon or graphite. Also, the particles can be composed of inorganic material, such as calcium phosphate, zinc polyphosphate or the like. Another type of granular microparticles consists of an inorganic core such as microporous silica gel with a microlayer of organic polymer. The pores and the surface of the grain may be modified in a way, that macromolecules are restricted from penetrating into the pores ("Restricted access material"). Also, the micro particles may consist of organic material such as a powder of cured resin, or highly crosslinked polysaccharides, as are available under the sephadex tradename, however care has to be taken in selecting an organic material in that it must not be soluble in the solvent used. The particles can be non-porous or porous, but preferably are porous with a preferred pore size in the range of 1 nm to 500 nm. Generally, the particles have a size from 5 nm to 80 mm, in particular from 0.5 mm to 30 mm, however porous microparticles preferably have a size of 1 mm or more, whereas nonporous microparticles preferably have a size of 1 mm or less. The microparticles can be pretreated, e.g., derivatized, such that the adsorbent properties thereof meet specific requirements. Any kind of commercially available adsorbent particles as used for solid phase extraction or chromatography, such as affinity chromatography with proteins, antibodies, peptides, carbohydrates, nucleic acids, or for ion exchange chromatography, immuno chromatography, hydrophobic interaction chromatography, chelating chromatography and reversed phase chromatography are useful. Materials suited for high performance liquid chromatography are especially useful. For example proteins, such as specific antibodies, lectins, avidin, receptor-proteins, enzymes, synthetic peptides, nucleic acids or oligonucleotides may be attached to the microparticles, either covalently or via linkers. The adsorbent particles have a granular shape, for example spherical. The microparticles may be used, e.g., in an amount of up to 50 mg, preferably 100 ng to 20 mg, per filter element.

In the final microparticle-containing filter element, the outer or inner surfaces of the enclosed microparticles are accessible to an applied liquid sample, and adsorption/immobilization of analytes contained in the liquid sample can take place.

Also, the method of the invention for producing a filter element by generating a microporous element can be performed within an aperture of a solid moisture-impervious support, comprising the steps of providing an aqueous solution of a hydrocolloid, which comprises solid microparticles slurried therein; applying the solution to the aperture so as to form a self-sustaining liquid layer over the cross-section of the aperture; causing the hydrocolloid solution to solidify; and, optionally, one or both of desiccating and crosslinking said layer of the solidified hydrocolloid solution.

Preferably, the hydrocolloid is selected from low melting agarose, starch, polyvinyl alcohol, and mixtures thereof. The aqueous solution of the hydrocolloid contains preferably 1 to 10% by weight, in particular 2 to 5% by weight of the solution, of the hydrocolloid. When polyvinyl alcohol is used as the hydrocolloid, the addition of up to 0,2% by weight of the solution, of sodium tetraborate or of up to 50% by weight of the solution, of dimethyl sulfoxide is sometimes advantageous.

These hydrocolloids are poorly soluble in cold water, however disperse or dissolve upon heating. Preferably, a hot hydrocolloid solution is applied to the aperture of the carrier. Upon cooling, the hydrocolloid solution solidifies.

In one alternative, the solidified hydrocolloid solution is subsequently desiccated. Desiccation can be accelerated by heating the arrangement to a temperature of about 40° C. Alternatively, in particular when using heat sensitive material, desiccation can be achieved by placing the arrangement in a closed chamber over a desiccating agent such as phosphorus pentoxide. The final moisture content preferably is less than 1 mbar water vapor partial pressure.

Upon desiccation, the solidified layer of hydrocolloid solution shrinks. In absence of the microparticles mentioned above, the solidified layer of hydrocolloid solution may shrink away from the inner wall of the support with the effect that no useful filter element would be obtained. According to the invention, microparticles are provided in the aqueous solution of hydrocolloid which act as pore-forming agent during desiccation. Accordingly, complete circumferential contact of the layer of hydrocolloid solution to the wall of the support is maintained and a plurality of microscopic cracks between the microparticles are formed upon desiccation. Also, the microparticles act so as to control or modify the adsorptive properties of the layer thus obtained. The microscopic cracks act as the liquid-permeable channels of the final microporous element. A proportion of 5 to 50%, calculated by weight of hydrocolloid solution, of microparticles will generally be useful.

The obtained layer of solidified hydrocolloid can be subjected to crosslinking instead of or after desiccation. For this purpose the microporous element is treated with crosslinking agents, e.g., boric acid, sodium tetraborate, phosphorus oxide chloride, epichlorhydrin or bisoxiranes, such as 1,4-butanediol diglycidyl ether. Polyvinylalcohol can be crosslinked with sodium tetraborate by applying alkaline pH for gelation. Both desiccation and crosslinking have the effect of increasing the mechanical stability and solvent-resistance of the final microporous element.

In a preferred method, an aqueous hydrocolloid solution, in particular an aqueous solution of low melting agarose, which comprises solid microparticles slurried therein is applied to the aperture of a solid moisture-impervious support so as to form a self-sustaining liquid layer over the cross-section of the aperture, then a channel-sparing nonsolvent is permeated through the liquid layer while retaining the layer by means of a retaining tool as explained in detail below, then the retaining tool is removed and the hydrocolloid solution is caused to solidify. Finally, the solidified hydrocolloid layer is preferably subjected to crosslinking.

Useful microparticles are those discussed above in connection with the first embodiment of the invention. Additionally, microparticles coated with dextran, such as dextran-coated charcoal, dextran-coated poly(styrene-divinyl benzene) or biological structures absorbed to a porous support, such as ribosomes, nucleosomes, chromosomes, synaptosomes, phages, plasmids, all preadsorbed to porous or non-porous supporting beads, are to be mentioned. The microparticles preferably have a size from 0.5 mm to 30 mm.

Further, the method of the present invention for producing a filter element by generating a microporous element can be performed within an aperture of a solid moisture-impervious support, comprising the steps of providing a solution of a monomer or a mixture of monomers in a solvent, optionally comprising crosslinking monomers, applying the solution to the aperture so as to form a self-sustaining liquid layer over the cross-section of the aperture; and causing the monomer (s) to polymerize.

Preferably, the monomers are ethylenically unsaturated monomers such as vinylacetate or other vinylesters, acrylic acid and its derivatives. Preferred acrylic acid derivatives include acrylic acid amides, such as acrylamide, N,N-dimethyl acrylamide, acrylic acid diamine monoamide; acrylic esters, such as butyl acrylate, dodecyl acrylate, octadecyl acrylate, vinyl acrylate, 2,3-epoxypropyl acrylate, diethylaminoethyl acrylate, 2-dimethylaminoethyl acrylate, and 3-sulfopropyl acrylate.

Crosslinking monomers are monomers having two or more sites of ethylenical unsaturation. A preferred crosslinking monomer is N,N'-methylenebis(acrylamide). The presence of crosslinking monomers increases the mechanical stability and solvent-resistance of the final microporous element.

As a solvent water, dimethyl sulfoxide, dimethylformamide, dimethylacetamide, formamide, formic acid, acetic acid, 2,2,2-trichloro ethanol, or mixtures thereof are useful, depending on the nature of the monomer(s) used.

In a preferred method, an aqueous solution of acrylic acid or its derivatives, preferably together with crosslinking monomers, which comprises solid microparticles slurried therein is applied to the aperture of a solid moisture-impervious support so as to form a self-sustaining liquid layer over the cross-section of the aperture, then a channel-sparing nonsolvent is permeated through the liquid layer while retaining the layer by means of a retaining tool as explained in detail below, then the retaining tool is removed and the acrylic acid (derivatives) caused to polymerize.

A proportion of 1 to 10% by weight of crosslinking monomer(s), for example N,N'-methylenebis(acrylamide), calculated on the total monomer, is generally useful.

Also a mixture of hydrophilic and hydrophobic monomers is useful. In this case, there will be interactions between the polymerized units of the hydrophobic monomers of the growing molecule chains, which result in the formation of a crystalline hydrophobic backbone of the polymer formed. The units of the hydrophilic monomers will be orientated towards the enclaves filled with the solvent. Accordingly, a microporous element is obtained where the liquid-permeable channels are predominantly hydrophilic.

Sometimes the monomer or mixture of monomers is soluble in the solvent, whereas the growing polymer becomes increasingly insoluble in the selected solvent and finally precipitates from the solution. A mixture of solvents may be useful in some instances. A nonsolvent can be caused to diffuse into the layer of polymer solution after polymerization, in order to precipitate the polymer formed or to complete precipitation of the polymer formed. Also, a porogenic liquid, such as n-dodecanol or polypropylene oxides, can be present during polymerization. The polymerization may also result in a polymer gel swelled with the solvent used.

Polymerization of the ethylenically unsaturated monomers is generally effected under the influence of free radicals. Free radicals are generated from the usual thermally decomposable initiators or a combination of free radical initiator and reducing agent. Usually, the initiator is added to the monomer solution. The concentration of the initiator is adjusted to provide sufficient pot life for application of the monomer solution to the aperture of the support. A combination of N,N'-tetramethyl ethylene diamine and a persulfate is especially preferred as initiator. In the alternative, an aqueous solution of initiator or initiator/reducing agent is used which is in contact by one or both sides of the liquid layer of monomer solution. Also photoinitiators such as riboflavin are useful for initiating the polymerization.

Instead of ethylenically unsaturated monomers, a monomer or mixture of monomers can be used which are capable of undergoing polyaddition or polycondensation. Among useful monomers are a combination of diamines with polyepoxides, such as a combination of ethylenediamine with 1,4-butanediol diglycidylether. Further examples include polypropylene oxide diamine and 1,4-butanediol, each with 1,4-butanediol diglycidyl ether.

This embodiment involves the benefit of a lower viscosity of the monomer solution compared to a solution of a polymer of the same monomers at a corresponding concentration. The lower viscosity facilitates application of the solution to the aperture of the support.

In order to modify the adsorptive properties of the microporous element, the monomer solution may further comprise solid microparticles. Microparticles that are useful, have been discussed above.

Where microparticles are used, it is sometimes advantageous to permeate the microparticle-containing liquid layer in the aperture of the support with a channel-sparing nonsolvent in order to displace excessive hydrocolloid solution, resin solution or monomer solution, respectively. The channel-sparing nonsolvent must be non-miscible with the solvents used. Permeation can be effected by pressing or drawing channel-sparing nonsolvent through the microparticle-containing layer whilst retaining the layer by means of a retaining tool consisting of a microporous filter. The hydrocolloid solution, resin solution or the monomer solution, respectively, is displaced from the larger interstices between the microparticles and accumulates at the points of contact of the microparticles. The channel-sparing nonsolvent keeps the interstices free, thus producing channels. The retaining tool is removed before solidification of the hydrocolloid or polymerization of the monomer(s) or precipitation of the resin. Upon solidification/polymerization/ precipitation, the microparticles are linked one to another at their points of contact. The channel-sparing nonsolvent is removed by washing with a suitable liquid. As channel-sparing nonsolvent, silicon oil is preferred.

Also possible are combinations of two or more of the embodiments discussed above. For example, a microparticle-containing layer could be prepared according to one embodiment and subsequently be impregnated with a resin solution, in which resin is precipitated according to one other embodiment.

Furthermore, the method of the present invention for producing microporous and filter elements of the invention may comprise the steps of providing a liquid suspension of microparticles; applying the liquid suspension to at least one microporous retainer; and causing solidification in spongy form of at least part of the suspension.

The microparticles may be linked together with each other and may be linked to the at least one microporous retainer under maintenance of microporosity.

The method according to the present invention for producing a filter element by generating a microporous element may comprise the steps of providing a solution of a synthetic or semi-synthetic resin in a solvent, including microparticles suspended therein; applying the solution to at least one microporous retainer; and causing a nonsolvent to diffuse into the layer, which nonsolvent is miscible with the solvent, whereby the synthetic resin precipitates to form the microporous element.

Preferably the resin is selected from the group consisting of polyvinyl esters, partially deacylated polyvinyl esters, cellulose derivatives, polyamides, and mixtures thereof. Among polyvinyl esters polyvinyl acetate, polyvinyl propionate, polyvinyl stearate, and polyvinyl cinnamic acid ester; among cellulose derivatives nitrocellulose, and cellulose propionate are to be mentioned. A suitable polyamide is Nylon 6/6.

In certain instances, the resin preferably comprises both hydrophilic and hydrophobic segments within its molecules. Suitable resins include poly(vinyl alcohol-co-ethylene), poly(vinyl alcohol-co-vinylacetate), ethylene acrylic acid copolymer, ethylene acrylic ester copolymer, ethylene acrylamide copolymer, acrylic acid vinylacetate copolymer, acrylamide vinylacetate copolymer, copolymer of acrylic acid diamine monoamide with vinylacetate, poly(vinyl alcohol-co-styrene), acrylamide acrylic ester copolymer, and mixtures thereof. Specifically, copolymers of acrylamide with hexyl acrylate, propyl acrylate or dodecyl acrylate are useful.

Preferably the solvent is selected from dimethyl sulfoxide, dimethylformamide, dimethylacetamide, formamide, formic acid, acetic acid, 2,2,2-trichloro ethanol, and mixtures thereof.

Preferably the nonsolvent is selected from water, alcohols having one to four carbon atoms, ammonia, ethylacetate, acetone, ethylenediamine, and mixtures thereof. The nonsolvent may be either liquid or gaseous.

The various methods of causing the nonsolvent to diffuse into the liquid layer of the resin solution will be exemplified with reference to a support having the form of a tube but will not be limited thereto. A liquid nonsolvent may be brought into contact with the liquid layer of resin solution from one or both sides thereof, for example by dipping the end of the tube at which the layer of resin solution is positioned into a liquid nonsolvent. Additionally or alternatively, nonsolvent may be introduced from the distant end of the tube. If a gaseous nonsolvent is to be used, the arrangement of support with layer of resin solution is positioned within an atmosphere which is saturated or nearly saturated with the vapors of the nonsolvent. Precipitation may also be accomplished in two successive steps by firstly applying gaseous nonsolvent and, after partial solidification, subsequently applying liquid nonsolvent.

Plane upper and lower surfaces of the microporous element are obtained when the final concentration of nonsolvent in the resin solution during precipitation is raised to about 50% by weight. A plane upper surface allows for a more uniform filtration performance of the filter element. A plane lower surface provides even contact with, for example, blotting membranes onto which an adsorbed material is to be transferred.

Typical combinations of resin/solvent/nonsolvent are, for example, one of poly(vinylalcohol-co-ethylene), nitrocellulose, cellulose propionate, or polyvinylacetate as resin, dimethyl sulfoxide as solvent and water as nonsolvent; or polyamides (like Nylon 6,6) as resin, 2,2,2-trichloro ethanol as solvent and acetone as nonsolvent.

Without intending to be bound to theory it is believed that in generating the microporous element according to this first embodiment of the present invention the following mechanisms are involved:

When the nonsolvent diffuses into the layer of resin solution, the solubility of the resin is gradually decreased. As the limit of solubility is reached the resin begins to precipitate from the solution at individual points. The precipitation of the resin proceeds at the points of initial precipitation. Ultimately, the solvent/nonsolvent is enclosed in large interconnecting enclaves in a solid matrix of resin. The interconnecting enclaves form the liquid-permeable channels of the final microporous element. If a synthetic resin is used which comprises both hydrophilic and hydrophobic segments, the hydrophobic segments will be forced towards each other and brought into contact with each other as the concentration of nonsolvent in the resin solution increases. There will be interactions between the hydrophobic segments of neighboring molecule chains, which result in the formation of a crystalline hydrophobic backbone of the precipitated resin. The hydrophilic segments will be oriented towards the enclaves filled with solvent/nonsolvent. Accordingly, a microporous element is obtained where the liquid-permeable channels are predominantly hydrophilic. This provides the benefit of biocompatibility. The term "biocompatibility" means that the three-dimensional structure of biopolymers, for example proteins, is maintained. The interphase forces are less destructive when the polymer surface is rich in hydroxyl, amide or ether groups.

In order to modify the adsorptive properties of the microporous element, the solution of the synthetic resin further comprises solid microparticles. The microparticles may be composed of silicon dioxide, silica gel, aluminum oxide, titan dioxide, zirconium oxide, glass, carbon or graphite. Also, the microparticles can be composed of inorganic material, such as calcium phosphate, zinc polyphosphate or the like. Another type of granular microparticles consists of an inorganic core such as microporous silica gel with a microlayer of organic polymer. The pores and the surface of the grain may be modified in a way, that macromolecules are restricted from penetrating into the pores ("restricted access material"). Also, the microparticles may consist of organic material such as a powder of cured resin, or highly crosslinked polysaccharides, as are available under the Superdex tradename, however care has to be taken in selecting an organic material in that it must not be soluble in the solvent used. The microparticles can be non-porous or porous, but preferably are porous with a preferred pore size in the range of 1 nm to 500 nm. Generally, the microparticles have a size from 5 nm to 500 $\mu$m, in particular from 0.5 $\mu$m to 30 $\mu$m, however porous microparticles preferably have a size of 1 $\mu$m or more, whereas non-porous microparticles preferably have a size of 1 $\mu$m or less. The microparticles can be pretreated, for instance derivatized, such that the adsorbent properties thereof meet specific requirements. Any kind of commercially available adsorbent particles as used for solid phase extraction or chromatography, such as affinity chromatography with proteins, antibodies, peptides, carbohydrates, nucleic acids, or for ion exchange chromatography, immuno chromatography, hydrophobic interaction chromatography, chelating chromatography and reversed phase chromatography are useful. Materials suited for high performance liquid chromatography are especially useful. For example proteins, such as specific antibodies, lectins, avidin, receptor-proteins, enzymes, synthetic peptides, nucleic acids or oligonucleotides may be attached to the microparticles, either covalently or via linkers. The adsorbent particles have a granular shape, for example spherical and/or with irregular surfaces, but not necessarily fibrillar.

In the final microparticle-containing filter element, the outer or inner surfaces of the enclosed microparticles are accessible to an applied liquid sample, and adsorption/immobilization of analytes contained in the liquid sample can take place.

Furthermore, the method of the present invention for producing a filter element by generating a microporous element may comprise the steps of providing an aqueous solution of a hydrocolloid, which comprises microparticles slurried therein; applying the solution to at least one microporous retainer; causing the hydrocolloid solution to solidify; and optionally, one or both of desiccating and crosslinking the solidified hydrocolloid solution.

Preferably, the hydrocolloid is selected from low melting agarose, starch, polyvinyl alcohol, and mixtures thereof. The aqueous solution of the hydrocolloid contains preferably 1 to 10% by weight, in particular 2 to 5% by weight of the solution, of the hydrocolloid. When polyvinyl alcohol is used as the hydrocolloid, the addition of up to 0.2% by weight of the solution, of sodium tetraborate or of up to 50% by weight of the solution, of dimethyl sulfoxide is sometimes advantageous.

These hydrocolloids are poorly soluble in cold water, however disperse or dissolve upon heating. Preferably, a hot hydrocolloid solution is applied to the aperture of the carrier. Upon cooling, the hydrocolloid solution solidifies.

In one alternative, the solidified hydrocolloid solution is subsequently desiccated. Desiccation can be accelerated by heating the arrangement to a temperature of about 40° C. Alternatively, in particular when using heat sensitive material, desiccation can be achieved by placing the arrangement in a closed chamber over a desiccating agent such as phosphorus pentoxide. The final moisture content preferably is less than 1 mbar water vapor partial pressure.

Upon desiccation, the solidified layer of hydrocolloid solution shrinks. In absence of the microparticles mentioned above, the solidified layer of hydrocolloid solution would shrink away with the effect that no useful filter element would be obtained. According to the invention, microparticles are provided in the aqueous solution of hydrocolloid which act as pore-forming agent during desiccation. Accordingly, a plurality of microscopic cracks between the microparticles are formed upon desiccation. Also, the microparticles act so as to control or modify the adsorptive properties of the layer thus obtained. The microscopic cracks act as the liquid-permeable channels of the final microporous element. A proportion of 5 to 50%, calculated by weight of hydrocolloid solution, of microparticles will generally be useful.

The obtained layer of solidified hydrocolloid can be subjected to crosslinking instead of or after desiccation. For this purpose the microporous element is treated with crosslinking agents, for instance boric acid, sodium tetraborate, phosphorus oxide chloride, epichlorhydrin or bisoxiranes, such as 1,4-butanediol diglycidyl ether. Polyvinylalcohol can be crosslinked with sodium tetraborate by applying alkaline pH for gelation. Both desiccation and crosslinking have the effect of increasing the mechanical stability and solvent-resistance of the final microporous element.

In a preferred method, an aqueous hydrocolloid solution, in particular an aqueous solution of low melting agarose, which comprises solid microparticles slurried therein is applied to a microporous retainer, then a channel-sparing nonsolvent is permeated through the liquid layer while retaining the layer by means of a retaining tool as explained in detail below, then the retaining tool is removed and the hydrocolloid solution is caused to solidify. Finally, the solidified hydrocolloid layer is preferably subjected to crosslinking.

Useful microparticles are those discussed above in connection with the first embodiment of the invention. Additionally, microparticles coated with dextran, such as dextran-coated charcoal, dextran-coated poly(styrene-divinyl benzene) or biological structures absorbed to a porous support, such as ribosomes, nucleosomes, chromosomes, synaptosomes, phages, plasmids, all preadsorbed to porous or non-porous supporting beads, are to be mentioned. The microparticles preferably have a size from 0.5 $\mu$m to 500 $\mu$m.

In addition, the method of the present invention for producing a filter element by generating a microporous element can comprise the steps of providing a solution of a monomer or a mixture of monomers in a solvent, optionally comprising crosslinking monomers; applying the solution to at least one microporous retainer; and causing the monomer (s) to polymerize.

Preferably, the monomers are ethylenically unsaturated monomers such as vinylacetate or other vinylesters, acrylic acid and its derivatives. Preferred acrylic acid derivatives include acrylic acid amides, such as acrylamide, N,N-dimethyl acrylamide, acrylic acid diamine monoamide; acrylic esters, such as butyl acrylate, dodecyl acrylate, octadecyl acrylate, vinyl acrylate, 2,3-epoxypropyl acrylate, diethylaminoethyl acrylate, 2-dimethylaminoethyl acrylate, and 3-sulfopropyl acrylate.

Crosslinking monomers are monomers having two or more sites of ethylenical unsaturation. A preferred crosslinking monomer is N,N'-methylenebis(acrylamide). The presence of crosslinking monomers increases the mechanical stability and solvent-resistance of the final microporous element.

As a solvent water, dimethyl sulfoxide, dimethylformamide, dimethylacetamide, formamide, formic acid, acetic acid, 2,2,2-trichloro ethanol, or mixtures thereof are useful, depending on the nature of the monomer(s) used.

In a preferred method, an aqueous solution of acrylic acid or its derivatives, preferably together with crosslinking monomers, which comprises solid microparticles slurried therein is applied to a microporous retainer, then a channel-sparing nonsolvent is permeated through the liquid layer while retaining the layer by means of a retaining tool as explained in detail below, then the retaining tool is removed and the acrylic acid (derivatives) caused to polymerize.

A proportion of 1 to 10% by weight of crosslinking monomer(s), for example N,N'-methylenebis(acrylamide), calculated on the total monomer, is generally useful.

Also a mixture of hydrophilic and hydrophobic monomers is useful. In this case, there will be interactions between the polymerized units of the hydrophobic monomers of the growing molecule chains, which result in the formation of a crystalline hydrophobic backbone of the polymer formed. The units of the hydrophilic monomers will be orientated towards the enclaves filled with the solvent. Accordingly, a microporous element is obtained where the liquid-permeable channels are predominantly hydrophilic.

Sometimes the monomer or mixture of monomers is soluble in the solvent, whereas the growing polymer becomes increasingly insoluble in the selected solvent and finally precipitates from the solution. A mixture of solvents may be useful in some instances. A nonsolvent can be caused to diffuse into the layer of polymer solution after polymerization, in order to precipitate the polymer formed or to complete precipitation of the polymer formed. Also, a porogenic liquid, such as n-dodecanol or polypropylene oxides, can be present during polymerization. The polymerization may also result in a polymer gel swelled with the solvent used.

Polymerization of the ethylenically unsaturated monomers is generally effected under the influence of free radicals. Free radicals are generated from the usual thermally decomposable initiators or a combination of free radical initiator and reducing agent. Usually, the initiator is added to the monomer solution. The concentration of the initiator is adjusted to provide sufficient pot life for application of the monomer solution to the microporous retainer. A combination of N,N'-tetramethyl ethylene diamine and a persulfate is especially preferred as initiator. In the alternative, an aqueous solution of initiator or initiator/reducing agent is used which is in contact by one or both sides of the liquid layer of monomer solution. Also photoinitiators such as riboflavin are useful for initiating the polymerization.

Instead of ethylenically unsaturated monomers, a monomer or mixture of monomers can be used which are capable of undergoing polyaddition or polycondensation. Among useful monomers are a combination of diamines with polyepoxides, such as a combination of ethylenediamine with 1,4-butanediol diglycidylether. Further examples include polypropylene oxide diamine and 1,4-butanediol, each with 1,4-butanediol diglycidyl ether.

This embodiment involves the benefit of a lower viscosity of the monomer solution compared to a solution of a polymer of the same monomers at a corresponding concentration. The lower viscosity facilitates application of the solution to the microporous retainer.

In order to modify the adsorptive properties of the microporous element, the monomer solution may further comprise solid microparticles. Microparticles that are useful, have been discussed above.

Where microparticles are used, it is sometimes advantageous to permeate the microparticle-containing liquid layer with a channel-sparing non-solvent in order to displace excessive hydrocolloid solution, resin solution or monomer solution, respectively. The channel-sparing nonsolvent must be non-miscible with the solvents used. Permeation can be effected by pressing or drawing channel-sparing nonsolvent through the microparticle-containing layer whilst retaining the layer by means of a retaining tool consisting of a microporous filter. The hydrocolloid solution, resin solution or the monomer solution, respectively, is displaced from the larger interstices between the microparticles and accumulates at the points of contact of the microparticles. The channel-sparing nonsolvent keeps the interstices free, thus producing channels. The retaining tool is removed before or after solidification of the hydrocolloid or polymerization of the monomer(s) or precipitation of the resin. Upon solidification/polymerization/precipitation, the microparticles are linked one to another at their points of contact. The channel-sparing nonsolvent is removed by washing with a suitable liquid. As channel-sparing nonsolvent, silicon oil is preferred.

Also possible are combinations of two or more of the embodiments discussed above. For example, a microparticle-containing layer could be prepared according to one embodiment and subsequently be impregnated with a resin solution, in which resin is precipitated according to one other embodiment.

In this context, the various methods according to the embodiments discussed above may also comprise the step of arranging at least one microporous membrane at the microporous retainer, wherein the microporous membrane is preferably formed of (regenerated) cellulose, polyamide, polyester, polypropylene (PP) or polytetrafluorethylene (PTFE).

In the various embodiments of the invention, the handling of very small liquid volumes is involved. Undesired evaporation of solvents before solidification can be avoided when all operations are performed in closed systems with solvent-saturated atmosphere. Preferably the temperature is precisely controlled.

The invention further relates to a filter element which is obtainable by the various embodiments discussed above and which comprises at least one microporous element including at least one microporous retainer and a spongy-form-polymer embedding microparticles and being linked to the at least one microporous retainer.

According to a preferred embodiment of the present invention, the microporous retainer, preferably comprising solid particles connected with each other and preferably being in the form of a disc, grid, large-pored membrane, membrane with supporting fabric, membrane with woven or unwoven characteristics, net, plate, rod and/or truncated cone (when being in the form of a membrane, the microporous retainer may comprise microparticles connected with each other), is formed of polyethylene (PE), polypropylene (PP), propylene/ethylene copolymer, polyvinyl acetate, polyamide, polystyrene, polyethylene terephthalate (PET), polyether etherketon (PEEK), polycarbonate, poly(vinyl alcohol-co-ethylene), polyester, polyamide, glass, ceramics, quartz, silicon, silicon nitride, or mixtures thereof, stainless steel, or composite materials thereof with fibers or frames of glass, silicon dioxide, carbon or ceramics.

In this context, it should be mentioned that it is possible to produce the microporous element in a (microporous) mold and to process and use it, optionally after adapting it to a suitable size for instance by cutting, in the desired ways described above and below.

According to an advantageous embodiment of the present invention, the polymer is attached to at least one part of the outer surface of the microporous retainer. Additionally or alternatively, the microporous retainer can contain in its pores the polymer in such a manner that the pores have residual free spaces forming channels allowing the flow of a fluid through the filter element. In this case, the average diameter of the microparticles is preferably less than 50% of the average diameter of the pores.

According to a particularly inventive embodiment of the present invention, at least one microporous membrane is arranged at the microporous retainer, the microporous membrane being preferably formed of (regenerated) cellulose, polyamide, polyester, polypropylene (PP) or PTFE.

The invention also pertains to an embodiment according to which the polymer comprises a resin. This resin can be selected from the group consisting of polyvinyl esters, partially deacylated polyvinyl esters, cellulose derivatives, polyamides, and mixtures thereof; or from the group consisting of poly(vinyl alcohol-co-ethylene), ethylene acrylic acid copolymer, ethylene acrylic ester copolymer, acrylamide vinylacetate copolymer, copolymer of acrylic acid diamine monoamide with vinylacetate, poly(vinyl alcohol-co-styrene), acrylamide acrylic ester copolymer, and mixtures thereof.

Alternatively, the polymer can comprise a solidified hydrocolloid solution, optionally desiccated or crosslinked, wherein the hydrocolloid is preferably selected from the group consisting of low melting agarose, starch, polyvinyl alcohol, and mixtures thereof.

Alternatively, the polymer can comprise the polymerization product of a monomer selected from the group consisting of vinylesters, acrylic acid and its derivatives; or the polymerization product of a diamine and a diepoxide.

According to a preferred embodiment of the present invention, the microporous element is arranged in a support member, which may have the form of a tube. In this context, at least one section of the tube may be of conical form, having a smaller and a larger cross-sectional end, and the microporous element may be located at or near to the smaller cross-sectional end.

According to an advantageous embodiment of the present invention, the outer and the inner surfaces of the microporous retainer are coated with a hydrophilic coating.

The inner wall of the tube can be coated with a hydrophilic coating, wherein it may be expedient to keep the edge of the tube next to the microporous element free of hydrophilic coating.

According to various particularly inventive embodiments of the present invention, the microporous element can be in the form of a disc, grid, membrane with supporting fabric, membrane with woven or unwoven characteristics, net, plate, rod, or truncated cone.

The invention finally relates to a multiple channel filter element, comprising a plurality of filter elements which are obtainable by the various embodiments discussed above.

In the various embodiments of the invention, the handling of very small liquid volumes is involved. Undesired evaporation of solvents before solidification can be avoided when all operations are performed in closed systems with solvent-saturated atmosphere. Preferably the temperature is precisely controlled.

The invention further relates to the filter elements which are obtainable by the various embodiments discussed above. The filter elements according to the invention can be applied for most versions of analytical or micro preparative liquid chromatography such as affinity chromatography, immuno chromatography, ion exchange chromatography, reverse phase chromatography, hydrophobic interaction chromatography, adsorption chromatography at silica gels as well as for binding studies enabling also the isolation of multi component binding complexes.

The filter elements may be especially useful in biotechnology, in molecular biology and in medical biochemical diagnostics, allowing low-cost screening of hundreds of samples in parallel.

The following advantages were achieved: The method prevents the dislocation of microparticles during processing of a liquid and also during transportation, improved or simplified by applying selected suitable techniques as described above. In addition to that, the method opens the way for far going miniaturization, avoids unspecific loss of biopolymer by presenting biocompatible surfaces, and saves cost by using expensive microparticle material in very small amounts. Transfer of separated substances from the filter to blotting membranes is possible without having problems with dead volumes. Production at low cost allows the filter to be used only once, avoiding the risk of contamination. The possibility of using microparticles with known or standardized adsorptive properties allows for the manufacture of filter elements with predictable adsorption characteristics and facilitates quality control.

These and other embodiments are disclosed or are obvious from and encompassed by the description and examples of the present invention. For example, further literature concerning any one of the methods, uses and compounds to be employed in accordance with the present invention may be retrieved from public libraries, using for example electronic devices. For example the public database "Medline" may be utilized which is available on Internet, e.g. under http://www.ncbi.nlm.nih.gov/PubMed/medline.html. Further databases and addresses are known to the person skilled in the art and can be obtained using, e.g., http://www.lycos.com. An overview of patent information in biotechnology and a survey of relevant sources of patent information useful for retrospective searching and for current awareness is given in Berks, TIBTECH 12 (1994), 352–364.

The present invention will be described in more detail below with reference to the exemplary embodiments which are schematically illustrated in the following drawings, in which.

Figure 1:
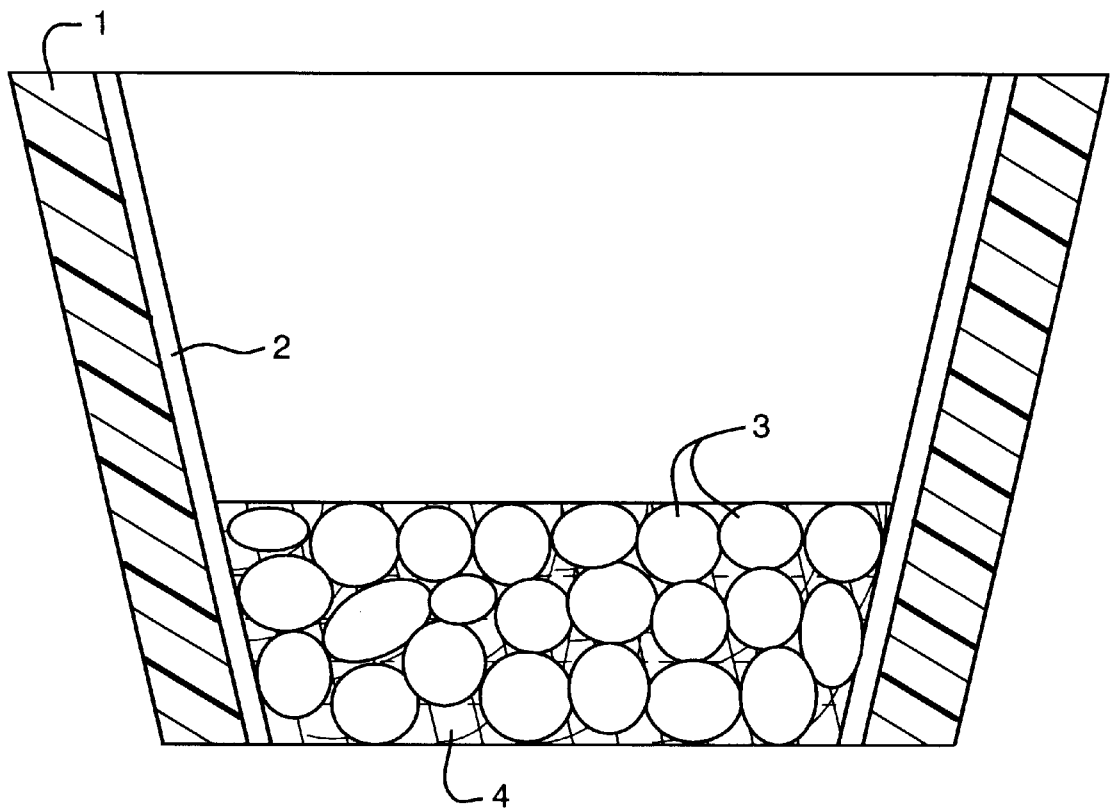
FIG. 1 shows a filter element obtained according to an embodiment of the invention.

FIG. 1 shows a filter element obtained according to an embodiment of the invention. The filter element comprises a moisture-impervious support (1) having a hydrophilic coating (2) at the inner wall thereof. The filter element further comprises microparticles (3) in a matrix (4) of precipitated resin, solidified hydrocolloid or polymerized monomer.

Figure 2:
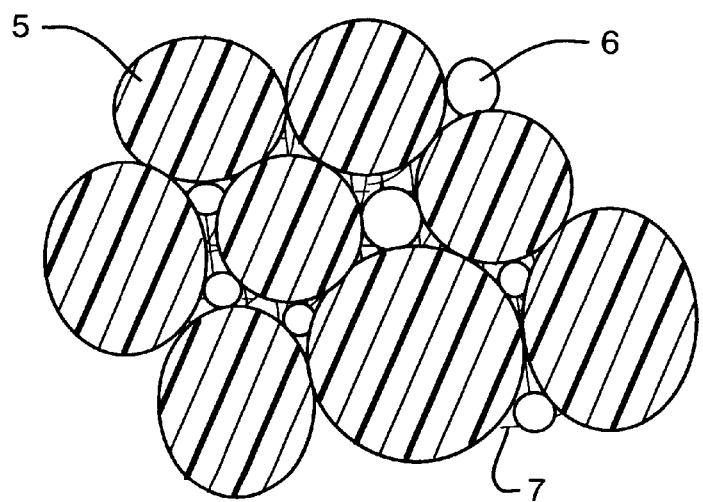
FIG. 2 illustrates the mode of operation of the channel-sparing nonsolvent.

FIG. 2 illustrates the mode of operation of the channel-sparing nonsolvent. The channel-sparing nonsolvent (6), shown in cross-section, keeps the larger interstices between the microparticles (5) free. The solution of resin, hydrocolloid or monomer (7) accumulates at the points of contact of the microparticles.

Figure 3:
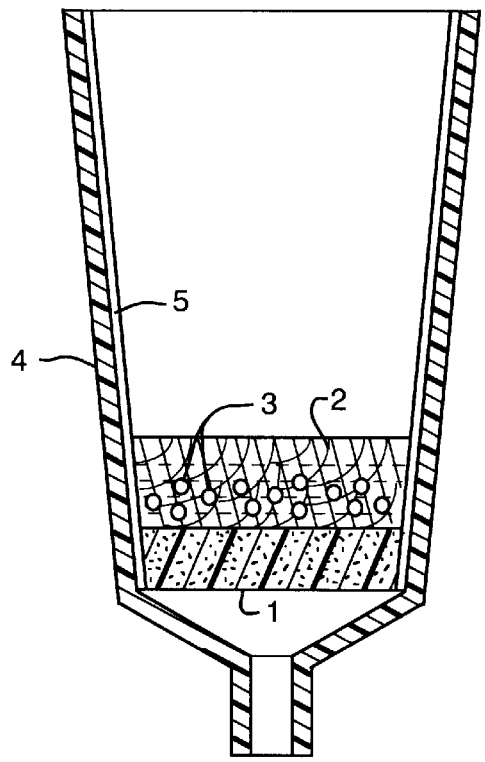
FIG. 3 shows a filter element obtained according to a first embodiment of the present invention.

FIG. 3 shows a filter element obtained according to a further embodiment of the present invention. The filter element comprises a microporous element including a microporous retainer 1 and a spongy-form-polymer 2 embedding microparticles 3 and being linked to the microporous retainer 1. In this context, FIG. 3 shows that the polymer 2 is attached to the top surface of the microporous retainer 1.

Though it cannot be explicitly taken from FIG. 3, it should be mentioned that the polymer 2 advantageously comprises a resin selected from the group consisting of polyvinyl esters, partially deacylated polyvinyl esters, cellulose derivatives, polyamides, polystyrene, poly(methyl methacrylate) and mixtures thereof. The resin may also be selected from the group consisting of poly(vinyl alcohol-co-ethylene), ethylene acrylic acid copolymer, ethylene acrylic ester copolymer, acrylamide vinylacetate copolymer, copolymer of acrylic acid diamine monoamide with vinylacetate, poly(vinyl alcohol-co-styrene), poly(styrene-co-maleic acid) and glycerol ester derivatives thereof, acrylamide acrylic ester copolymer, and mixtures thereof. Alternatively, the polymer 2 comprises a solidified hydrocolloid solution, optionally desiccated or crosslinked, wherein the hydrocolloid can be selected from the group consisting of low melting agarose, starch, polyvinyl alcohol, and mixtures thereof. Finally, it should not be overseen that the polymer 2 can also comprise the polymerization product of a monomer selected from the group consisting of vinylesters, acrylic acid and its derivatives; or the polymerization product of a diamine and a diepoxide.

The microporous element, as shown in FIG. 3, can be generated in situ from a liquid precursor. The liquid precursor readily takes a shape that matches the shape of the inner surface of a moisture-impervious support member 4 as well as the shape of the microporous retainer 1. Any imperfections like burrs etc. of the aperture of the moisture-impervious support member 4 are hereby compensated for. Upon solidification, a microporous element is obtained, which snugly fits into the aperture of the support member 4 and has complete circumferential contact to the walls thereof.

Preferably, the support member 4 is formed of a plastic such as polypropylene (PP), polyethylene (PE), propylene/ethylene copolymer, polyvinyl acetate, polyamide, polystyrene, polyethylene terephthalate (PET), polyether etherketon (PEEK), polycarbonate, polyethylene vinylacetate, poly(vinyl alcohol-co-ethylene), polyester, polyamide, glass, ceramics, quartz, silicon nitride, or mixtures thereof. Also included are composite materials of plastic with fibers or frames of glass, silicon dioxide, carbon or ceramics.

As can be taken from FIG. 3, the support member 4 has the form of a tube, preferably with circular cross-section, and the microporous element is generated at or near to one edge of the tube. In order to facilitate sample application and for accommodation of greater sample volumes, preferably at least a section of the tube is of conical form, having a smaller and a larger cross-sectional end, with the microporous element generated at or near to the smaller cross-sectional end. For example, the support member 4 is a pipette tip such as commonly used with Eppendorf pipettes. In order to prevent dislocation, such as slipping, of the microporous element formed, the tube may have a structured inner surface, like a surface with rings or grooves.

It is also envisaged to arrange a plurality of support members 4, for example up to several hundreds, in parallel alignment to form a multiple channel filter element. The multiple channel filter element will allow a biological sample to be tested simultaneously against hundreds of reagents. Alternatively, the support member 4 can comprise a plurality of apertures, for instance in the form of parallel bores or tapered holes. When the multiple channel element is to be evaluated optically, it is convenient to include an opacifying agent such as carbon black into the support member material to prevent interference from neighboring channels.

There are several possibilities of applying the liquid phase to the aperture of the support member 4. The various methods will be exemplified with reference to a tubular support member 4 but will not be limited thereto. As the liquid phase in general is a solution the terms "liquid phase" and "solution" will be used interchangeably unless otherwise required by the context. Conveniently, application of the solution to the aperture is accomplished by capillary action. The support member 4, for example a tube, is dipped into the solution and raised again. Due to the surface tension of the solution, a liquid layer will remain in the aperture over the cross-section of the aperture. If, for example, the viscosity of the solution is too high different methods for applying the solution to the aperture may be adopted. The ascending force of the solution may be enhanced by temporarily sealing the distant end of the tube, slightly heating the tube, then dipping the tube with its free end into the solution, and allowing the tube to cool to ambient temperature, whereby the solution is drawn into the tube by the volume contraction of the enclosed air. Alternatively, the solution can be introduced from the distant end of the tube and may be brought into its final position by centrifugation. Preferably, the end at or near to which the microporous element is to be formed is sealed with a cap or by pressing against an elastic plate. The cap or the elastic plate preferably has microgrooves or micropores for allowing the enclosed air to escape. Then the arrangement is subjected to centrifugation during which the solution migrates to the end of the tube where it is retained at least partially by the cap or elastic plate. The cap or the elastic plate may be removed before or after solidification, in particular before solidification of the solution or of a part of the solution.

The practitioner often faces the problem that aqueous samples that are introduced in containers made of hydrophobic material tend to adhere to the wall in drops rather than flowing down and collecting at the bottom. In order to avoid this phenomena, the inner wall of a tube which acts as support member 4 for a filter element according to the invention, may be coated with a hydrophilic coating 5. The hydrophilic coating 5 will prevent aqueous samples from adhering to the wall of the support member 4. Also, there is no adsorptive loss of biopolymers due to adsorption to the wall of the support member 4. If the inner wall of the tube is coated with the hydrophilic coating 5, the edge of the tube next to the microporous element is preferably kept free of hydrophilic coating 5. This will prevent sample liquids which exit from the edge of the tube next to the microporous element from creeping to adjacent filter elements, especially in the embodiment of the present invention where a plurality of filter elements is arranged to form a multiple channel filter element.

The hydrophilic coating 5 is conveniently prepared by applying a solution of one or more polyvinyl esters in an organic solvent to the inner wall of the tube, allowing the organic solvent to evaporate, and partially hydrolyzing the resulting layer of polyvinyl ester at the surface thereof. Suitable polyvinyl esters include polyvinyl acetate (a MW of about 500000 is generally suitable), polyvinyl propionate and polyvinyl stearate.

Partial hydrolysis of the layer of polyvinyl ester is performed by contacting the layer of polyvinyl ester with an alkaline aqueous solution, such as sodium hydroxide. The edge of the tube next to the microporous element can be kept free of hydrophilic coating 5 by applying the solution of polyvinyl ester only to a part of the inner wall of the tube, for example by partially immersing the tube into the solution of polyvinyl ester. After hydrolysis, the microporous element can be generated at or near to the edge of the tube, that has not been brought into contact with the polyvinyl ester solution. Alternatively, the entire inner wall of the tube can be coated with polyvinyl ester, but only part thereof is hydrolyzed.

Alternatively, the hydrophilic coating 5 can be generated by using a high molecular weight polypropylene glycol, for example having a molecular weight of 4000 or higher. Such polypropylene glycols show moderate to good solubility in cold water, however poor solubility in warm water. Accordingly, a cold aqueous solution of polypropylene glycol, for example at 0° C. to 4° C., might be introduced into the tube and subsequently the temperature is raised, for instance to about 20° C. The polypropylene glycol coming out of the solution shows a high affinity to the inner wall of the tube and deposits thereon as a thin layer. Excess polypropylene glycol solution is then removed. Additional chemical crosslinking may be advantageous in some cases.

Figure 4:
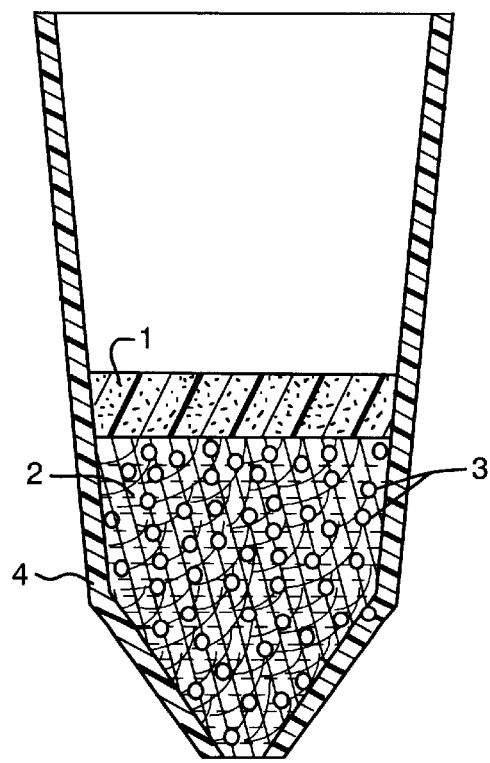
FIG. 4 shows a filter element obtained according to a second embodiment of the present invention.

FIG. 4 shows a filter element obtained according to an embodiment of the present invention. The filter element comprises a microporous element including a microporous retainer 1 and a spongy-form-polymer 2 embedding microparticles 3 and linked to the microporous retainer 1. In this context, FIG. 4 shows that the polymer 2 is attached to the bottom surface of the microporous retainer 1.

It can be taken from FIG. 4 that the microporous element is arranged in a moisture-impervious support member 4 having the form of a tube. One section of the tube is of conical form, having a smaller and a larger cross-sectional end, and the microporous element is located at or near to the smaller cross-sectional end.

Figure 5:
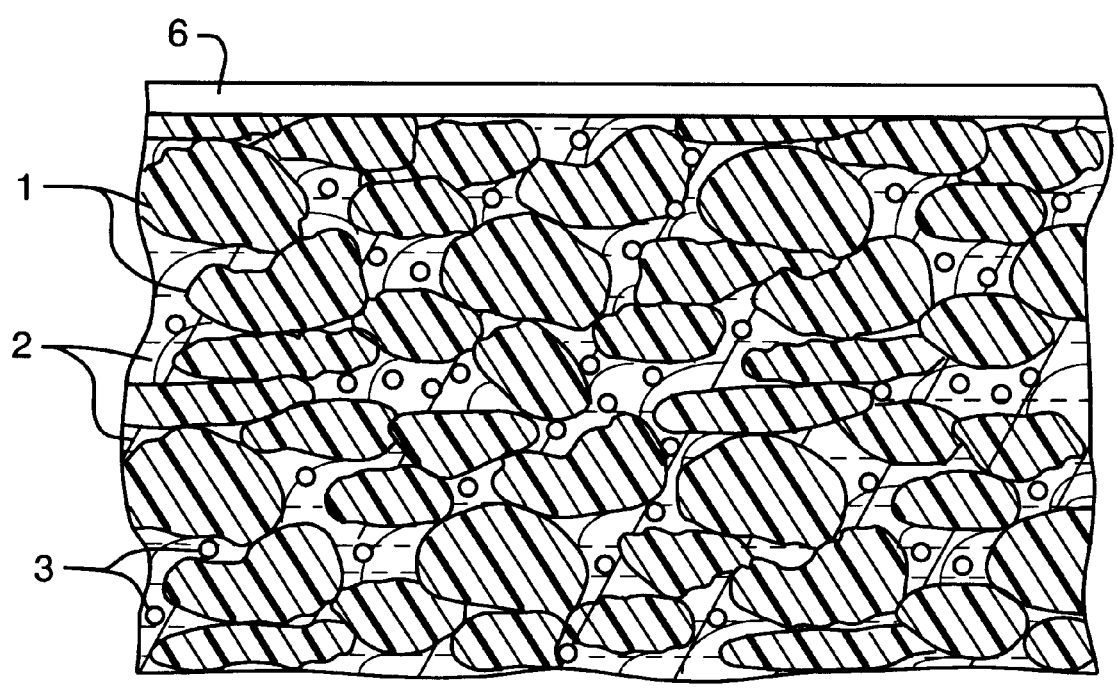
FIG. 5 shows a filter element obtained according to a third embodiment of the present invention.

FIG. 5 shows a filter element obtained according to another embodiment of the present invention. It is illustrated in FIG. 5 that the microporous retainer 1 comprises solid particles connected with each other.

Though it cannot be explicitly taken from FIG. 5, it should be mentioned that the microporous retainer 1 is advantageously formed of polyethylene (PE), polypropylene (PP), propylene/ethylene copolymer, polyvinyl acetate, polyamide, polystyrene, polyethylene terephthalate (PET), polyether etherketon (PEEK), polycarbonate, poly(vinyl alcohol-co-ethylene), polyester, polyamide, glass, ceramics, quartz, silicon, silicon nitride, or mixtures thereof, stainless steel, or composite materials thereof with fibers or frames of glass, silicon dioxide, carbon or ceramics. In this context, the microporous retainer 1 can be embodied in the form of a disc, grid, large-pored membrane, membrane with supporting fabric, membrane with woven or unwoven characteristics, net, plate, rod and/or truncated cone. When being in the form of a membrane, the microporous retainer 1 may comprise microparticles connected with each other.

In this context, it should be mentioned that it is possible to produce the microporous element in a (microporous) mold and to process and use it, optionally after adapting it to a suitable size for instance by cutting, in the desired ways described above and below.

FIG. 5 shows that the microporous retainer 1 contains in its pores the polymer 2 in such a manner that the pores have residual free spaces forming channels allowing the flow of a fluid through the filter element. In this connection, the average diameter of the microparticles 3 is less than 50% of the average diameter of the pores.

A microporous membrane 6 is arranged at the top surface of the microporous retainer 1. Though it cannot be explicitly taken from FIG. 5, it should be mentioned that the microporous membrane 6 is advantageously formed of (regenerated) cellulose, polyamide, polyester, polypropylene (PP) or teflon.

Figure 6:
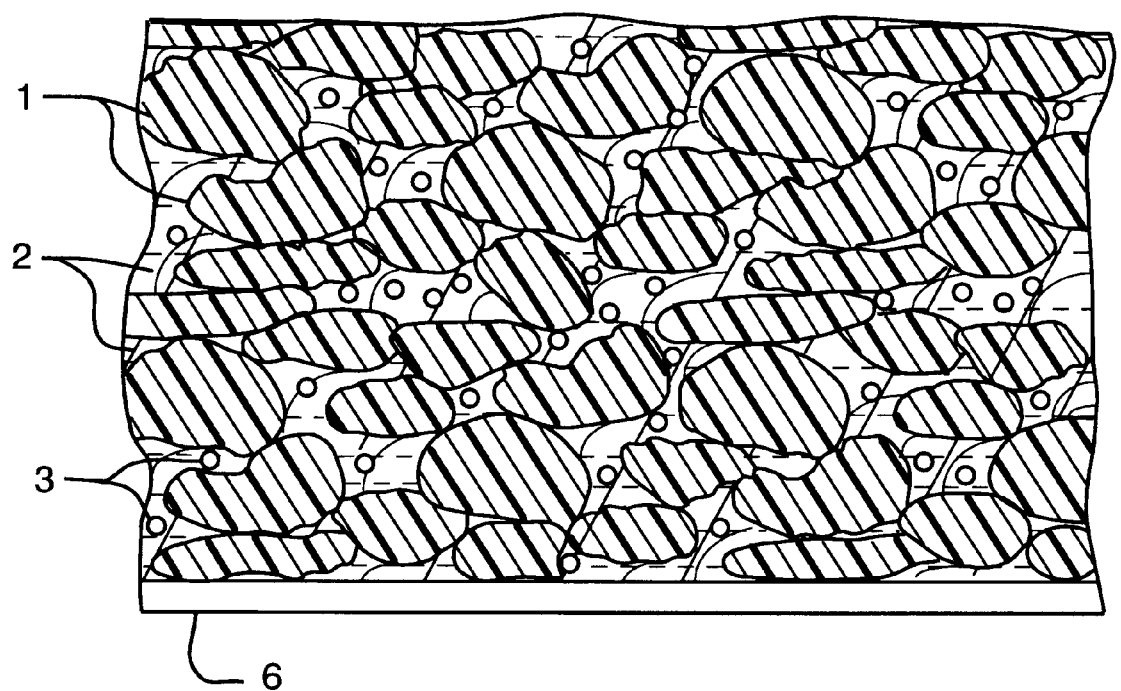
FIG. 6 shows a filter element obtained according to a fourth embodiment of the present invention.

FIG. 6 shows a filter element obtained according to a further embodiment of the present invention. In FIG. 6, the microporous membrane 6 is arranged at the bottom surface of the microporous retainer 1.

The invention will now be further illustrated by the following examples.

Microfilters of example 1–4 are less resistant to organic solvents but more easy to prepare. Microfilters of example 5 and 6 are especially useful when labile macromolecules such as enzymes, antibodies or receptor proteins are bound to microparticles. The solidification occurs under biocompatible conditions with respect to temperature, acidity and tonicity. Microfilters of example 7 are especially useful for covalent immobilization.

In this context, microfilters of example 12 and 13 are especially useful when labile macromolecules such as enzymes, antibodies or receptor proteins are bound to microparticles. The solidification occurs under biocompatible conditions with respect to temperature, acidity and tonicity. Microfilters of example 14 are especially useful for covalent immobilization. Microfilters of example 15 are useful when organic solvents are applied.

EXAMPLE 1

Production of Biocompatible Surface of the Impermeable Element and Production of Microporous Element by Diffusion of Nonsolvent A solution of 3% polyvinyl acetate (w/v) in acetone (MW 500000, Cat. No. 38793-2; Aldrich, Steinheim G) was applied to the inner surface of a 1 ml-pipet tip (Cat. No. 00 30 001.311 Eppendorf, Hamburg G) and was drained over blotting paper. After evaporating at ambient temperature and heating at 70° C. overnight, the tip was filled with 1 ml of 1 N—NaOH in water, and a partial reaction was performed at 24° C. for 30 min. Finally, the tip was washed and dried. In addition, a liquid phase was prepared, by dissolving 1 g of poly (vinyl alcohol-co-ethylene) of 44 mol % ethylene content (Cat. No. 41, 410-7; Aldrich, Steinheim G.) with 4 ml dimethyl sulfoxide at 100° C. A volume of 3 $\mu$l of liquid phase was taken up at 40° C. After closing the smaller aperture of the pipet tip, water was introduced into the tip as a vapor. One hour later, 50 $\mu$l of water was applied directly over the solidifying liquid phase to obtain further diffusional precipitation. The flow rate of the thus obtained filter element was 5.3 $\mu$l/min (0.8 mm aperture; 500 mbar).

EXAMPLE 2

Production by Precipitation of Resin with Inclusion of Microporous Beads

100 $\mu$g of reversed-phase material on silica gel ($C_{18}$, 30 nm pore, 5 $\mu$m bead; Vydac, Hesperia, Calif., USA) was sonicated with the polymer solution (see example 1). This liquid phase was then treated further as described under example 1. The flow rate was 1 μl/min (aperture 0.8 mm; 1 bar). With silicon dioxide (fumed silica, 14 nm size; Cat. No. S-5505, Sigma, Deisenhofen G.) as adsorbent, instead of reversed-phase material, the flow-rate was 240 nl/min.

EXAMPLE 3
Production by Precipitation of Semisynthetic Polymer with Inclusions of a Mixture of Different Types of Microparticles A mixture was prepared from three different types of porous microparticles: 100 mg of anion exchanger based on silica gel (Adsorbex-SAX, Cat. No. 19845; Merck, Darmstadt G.) 100 mg of cation exchanger (Adsorbex-SCX, Cat. No. 19846) and 100 mg reversed-phase RP8 (Cat. No. 9362). After sonification with 1 ml of dimethyl sulfoxide and centrifugation, the wet sediment was supplemented with 600 μl of 15% cellulose propionate (average MW 200 000; Cat. No. 18462-4; Aldrich, Steinheim, G.) in dimethyl sulfoxide, prepared at 95° C. A modified Comfortip (Cat. No. 30061; Eppendorf, Hamburg G) with biocompatible surface modification was held pressed against the microporous-retainertool, filled with 35 μl of liquid and layered with 80 μl of silicon oil and finally layered with 200 μl distilled water. Positive pressure (at least 2 bar) was applied until the water phase passed finally the microfilter. The flow rate was 10 μl/min. (1.5 mm aperture, 12 mm length; 7 mbar).

EXAMPLE 4
Production by Precipitation of Semisynthetic Polymer in the Nanoliter Range A volume of 200 nl of a 20% solution of cellulose propionate (MW 200,000) in dimethyl sulfoxide (w/v) was introduced into a gel loader tip (Cat. No. 00 30 001.222; Eppendorf, Hamburg G). The aperture was closed temporarily with silicon oil, and nonsolvent was introduced as a vapor from the other side. The flow rate was 1.5 μl/min (aperture 80 μm; 100 mbar).

EXAMPLE 5
Production by Crosslinking of Reversible Hydrogel in the Presence of Channel-sparing Nonsolvent at 0° C.

A solution of 5% (w/v) poly(vinyl alcohol) (MW 124 000–186 000, 99% hydrolyzed; Cat. No. Aldrich, 36 306-5; Steinheim G.) in water was prepared at 100° C. 4 ml of solution were mixed with 1 ml of 50 mM sodium tetraborate pH 4.7 and cooled to 0° C. Finally, 1 g of enzyme-containing SAX particles (Adsorbex-SAX, Merck, Darmstadt G.) were added. 40 μl of this liquid-phase were filled into a modified Comfortip with a biocompatible surface. The tip was pressed against a microporous-retaining tool (see example 7) and was layered with 50 μl silicon oil. After applying positive pressure, migration of the silicon oil was achieved into the granular bed. In order to achieve crosslinking, a final layer of 50 mM sodium tetraborate pH 8.6 solution was forced through the Comfortip. The flow rate was 0.5 μl/min (1.3 mm aperture; 7 mbar).

EXAMPLE 6
Production by Using a Reversible Hydrogel in the Presence of a Channel-sparing Non-solvent One gram of DEAE-Si 300, 10 μm-size (Cat. No. 43536; Serva, Heidelberg G) was mixed with 5 ml of a 2% agarose solution at 40° C. The agarose (low melt preparative agarose; Cat. No. 162-0017; Bio-Rad Munich, G) had been dissolved at 90° C. in 3% sucrose solution. Then, 100 μl of liquid phase was taken up into a modified standartip with biocompatible surface coating, as described before (Standartip Cat. No. 30.003.004; Eppendorf, Hamburg G). The standartip was held pressed against the microporous retaining tool, as described under example 7. After addition of an upper layer of 200 μl silicon oil at 40° C., positive pressure was applied until 150 μl had passed into the microporous retaining tool. After removal of the tool, solidification was achieved at 6° C. Finally the silicon oil was expelled by filtration of 500 μl sucrose solution. The filtration rate was 7 μl/min (aperture 0.5 mm; 7 mbar).

EXAMPLE 7
Production by Polycondensation in Presence of Channel-sparing Nonsolvent 100 mg of silica gel (Lichrosorb Si 100, 7 μm size; Cat. No. 9340; Merck, Darmstadt, G.) were sonicated with 500 μl of monomer solution (by vol: 5 parts of 1,4-butanediol diglycidyl ether (Cat. No. 22,089-2; Aldrich, Steinheim G.), one part dimethyl sulfoxide and one part ethylenediamine). 35 μl of liquid phase were taken up into a modified Comfortip (Cat. No. 30061; Eppendorf, Hamburg G). The filled Comfortip was held pressed against a retaining tool consisting of a microporous metal sieve (Cat. No. 12550812; Bischoff, Leonberg) located on a 3 mm thick filter paper (Cat. No. 2727; Schleicher and Schull, Dassel, G). After layering 80 μl of silicon oil onto the liquid-phase, positive pressure was applied (at least one bar) until 30 μl of silicon oil were flown through the Comfortip. After removal from the retaining tool, solidification was achieved by curing in a closed system. Finally, the micro filter was washed with distilled water and suitable buffer. The flow rate was 32 μl/min (1,3 mm aperture; 1 bar).

When using nonporous silicon dioxide (1–5 μm, Cat. No. S-56631; Sigma, Deisenhofen G.) instead of silica gel as adsorbent, the flow rate was 1 μl/min (aperture 1.5 mm; volume 10 μl, Comfortip 1 bar).

EXAMPLE 8
Production of Biocompatible Surface of the Impermeable Element and Production of Microporous Element by Diffusion of Nonsolvent A solution of 3% polyvinyl acetate (w/v) in acetone (MW 500,000, Cat. No. 38793-2; Aldrich, Steinheim G) was applied to the inner surface of a 100 μl-filtertip (Cat. No. 00 30 067.010; Eppendorf, Hamburg G) and was drained over blotting paper. After evaporating at ambient temperature and heating at 70° C. overnight, the tip was filled with 1 ml of 1 N–NaOH in water, and a partial reaction was performed at 24° C. for 30 min. Finally, the tip was washed and dried. In addition, a solution was prepared, by dissolving 1 g of poly(vinyl alcohol-co-ethylene) of 44 mol % ethylene content (Cat. No. 41, 410-7; Aldrich, Steinheim G) with 4 ml dimethyl sulfoxide at 100° C. 100 mg of reversed-phase material on silica gel ($C_{18}$, 30 nm pore, 5 μm bead; Vydac, Hesperia, Calif., USA) was sonicated with the polymer solution. A volume of 30 μl of suspension was taken up at 40° C. After closing the smaller aperture of the filtertip, water was introduced into the tip as a vapor. One hour later, 50 μl of water was applied directly over the solidifying liquid phase to obtain further diffusional precipitation.

EXAMPLE 9
Inclusion of Microparticles into a Microporous Retainer

A solution of poly-(vinyl acetate) (Cat. No. 38793-2; Aldrich, Steinheim G) was prepared using 1 g of poly-(vinyl acetate) and 19 ml of acetic acid. A suspension of microparticles (Cibacron blue F3GA; Si 300 polyol, 5 μm; Cat. No. 43532; Serva, Heidelberg G) was obtained using 1 g of particles and 4 ml of solution. The suspension was applied to a disc of polypropylene frit (porosity 0) which was placed on a porous teflon membrane held flat on a vacuum suction device. When filtration was completed, water was added for formation of spongy-form-polymer.

The microporous element thus formed was inserted and held in the support under radial compression.

EXAMPLE 10
Production by Precipitation of Semisynthetic Polymer with Inclusions of a Mixture of Different Types of Microparticles A mixture was prepared from three different types of porous microparticles: 100 mg of anion exchanger based on silica gel (Adsorbex-SAX, Cat. No. 19845; Merck, Darmstadt G) 100 mg of cation exchanger (Adsorbex-SCX, Cat. No. 19846) and 100 mg reversed-phase RP8 (Cat. No. 9362). After sonication with 1 ml of dimethyl sulfoxide and centrifugation, the wet sediment was supplemented with 600 $\mu$l of 15% cellulose propionate (average MW 200,000; Cat. No. 18462-4; Aldrich, Steinheim, G) in dimethyl sulfoxide, prepared at 95° C. A modified 100 $\mu$l -filtertip (Cat. No. 00 30 067.010; Eppendorf, Hamburg G) with biocompatible surface modification was filled with 20 $\mu$l of liquid and layered with 30 $\mu$l of silicon oil and finally layered with 50 $\mu$l distilled water. Positive pressure was applied until the water phase passed finally the microfilter.

EXAMPLE 11
Preparation of a Microporous Element Using a Prefabricated Composite Membrane with Integrated Supporting Web as Retainer 1 g of poly(vinyl alcohol-co-ethylene) (Cat. No. 41409-3; Aldrich, Steinheim G) was dissolved with 9 ml of dimethyl sulfoxide. 1 g of silica gel (20 $\mu$m, 60 nm; Merck, Darmstadt G) was suspended therein. 3 ml of suspension was warmed up to 60° C. and was evenly distributed over the membrane (regenerated cellulose on polypropylene web; Cat. No. U 3880; Sigma, Deisenhofen G) and held flat on a vacuum filtration device on a plane frit. After completing filtration, finally water was applied for solidification. Discs were cut with a cutting device for insertion into a hollow support.

EXAMPLE 12
Production by Crosslinking of Reversible Hydrogel in the Presence of Channel-sparing Nonsolvent at 0° C.

A solution of 5% (w/v) poly(vinyl alcohol) (MW 124 000–186 000, 99% hydrolyzed; Cat. No. Aldrich, 36 306-5; Steinheim G) in water was prepared at 100° C. 4 ml of solution were mixed with 1 ml of 50 mM sodium tetraborate pH 4.7 and cooled to 0° C. Finally, 1 g of enzyme-containing SAX particles (Adsorbex-SAX, Merck, Darmstadt G) were added. 100 $\mu$l of this suspension were filled into a modified 1 ml-filtertip (Cat. No. 00 30 067.037; Eppendorf, Hamburg G) with a biocompatible surface. The tip was layered with 100 $\mu$l silicon oil. After applying positive pressure, migration of the silicon oil was achieved into the granular bed. In order to achieve crosslinking, a final layer of 50 mM sodium tetraborate pH 8.6 solution was forced through the microporous element.

EXAMPLE 13
Production by Using a Reversible Hydrogel in the Presence of a Channel-sparing Non-solvent 1 g of DEAE-Si 300, 10 $\mu$m-size (Cat. No. 43536; Serva, Heidelberg G) was mixed with 5 ml of a 2% agarose solution at 40° C. The agarose (low melt preparative agarose, Cat. No. 162-0017; Bio-Rad, Munich, G) had been dissolved at 90° C. in 3% sucrose solution. Then, 100 $\mu$l of liquid phase was taken up into a modified 1 ml-filtertip (Cat. No. 00 30 067.037; Eppendorf, Hamburg G) with biocompatible surface coating, as described in example 8. After addition of an upper layer of 500 $\mu$l silicon oil at 40° C., positive pressure was applied until 400 $\mu$l had passed the microporous retainer. Solidification was achieved at 6° C. Finally the silicon oil was expelled by filtration of 500 $\mu$l sucrose solution.

EXAMPLE 14
Production by Polycondensation in Presence of Channel-sparing Nonsolvent 100 mg of silica gel (Lichrosorb Si 100, 7 $\mu$m size; Cat. No. 9340; Merck, Darmstadt, G) were sonicated with 500 $\mu$l of monomer solution (by vol: 5 parts of 1,4-butanediol diglycidyl ether (Cat. No. 22,089-2; Aldrich, Steinheim G), one part dimethyl sulfoxide and one part ethylenediamine). 35 $\mu$l of liquid phase were taken up into a modified 10 $\mu$l-filtertip (Cat. No. 00 30 067.002; Eppendorf, Hamburg G). After layering 70 $\mu$l of silicon oil onto the liquid-phase, positive pressure was applied (at least one bar) until 30 $\mu$l of silicon oil were flown through the filtertip. Solidification was achieved by curing in a closed system. Finally, the filter element was washed with distilled water and suitable buffer.

EXAMPLE 15
Production by Polymerization in the Presence of Channel-sparing Nonsolvent 100 mg of silica gel type anion exchanger of HPLC quality (DEAE-Si 300, 10 $\mu$m; Cat. No. 43536; Serva, Heidelberg G) were sonicated with ice-cold 500 $\mu$l monomer solution (By weight: 26% acrylamide; 0.7% bis acrylamide; 170 mM Tris HCl pH 8.8; 0.05% tetramethyl ethylenediamine (Cat. No. 8133; Sigma, Deisenhofen) 0.08% sodium persulfate).

All further steps were done as described in example 14 except that the temperature was held between 0° C. and 2° C. as during the flushing step with silicon oil. Finally, solidification was achieved by curing at 45° C.

EXAMPLE 16
Production Using Hydrogel and Microparticles with Reformation of Channels by Means of Drying 1 ml of a 2% (w/v) solution of agarose (Bio-Rad, Munich G) was mixed and sonicated with 200 mg of microporous titan dioxide (YMC-Gel, TIAOS 20 NP; YMC Europe, Schermbeck G) at 40° C. At the same temperature, 50 $\mu$l of liquid was taken up into a filtertip that was provided with biocompatible surface coating (see example 8). Using low speed centrifugation (80 rounds per minute) in a swing-out-rotor, the pressure was adjusted in a way that flow was stopped when the microparticles were just beginning to be exposed. Solidification was achieved at 6° C. Drying was done at ambient temperature and finally over $P_2O_5$, at 1 mb.

EXAMPLE 17
Isolation of Multimolecular Complexes Consisting of Oligonucleotides and Specific Macromolecules, Noncovalently Bound Together A labeled oligonucleotide probe was incubated with nuclear extract, and 8 $\mu$l were filtered over a polyacrylamide—DEAE microfilter (example 15) which was washed with 40 $\mu$l buffer. The free oligonucleotide was retained and the complexed form was obtained in the eluate within some minutes.

EXAMPLE 18
Production of a Multi-column Multi-channel Plate

A 5% solution of poly-(vinylalcohol-co-ethylene) (Cat. No. 41, 408-5, Aldrich, Steinheim, G.) was prepared under reflux using the solvent mixture of two nonsolvents, i.e. 70 volumes of n-propanol, 30 volumes of water and 10 volumes of dimethyl sulfoxide. One g of Ni-NTA Silica, 16–24 μm size (Cat. No. 30710; QIAGEN GmbH, Hilden, G.) was suspended in 4 ml of polymer solution. As a support, a 384-channel plate had been prepared by CAM, starting with a 384-well plate (GENETIX Well, Cat. No. X 5005; Dunn, Thelenberg, G.). The free ends of the channels, 1.5 mm in diameter, were closed by applying pressure against a flexible microporous retainer sheet, 1 cm thick. Aliquots of 35 μl were filled in to each channel. Due to capillar activity of this assembly, all excess fluid was drained off until the solution was in line with the top zone of the particle bed. Thereafter, the retainer was removed and, evaporation and solidification were achieved at ambient temperature for one hr. Finally, 50 μl of distilled water was applied for 5 hrs.

EXAMPLE 19
Production of a Microporous Frit by Sintering Two Size Fractions of Low-melting Polymer Ordered in Two layers, Applicable for Sieving Out of Cell Debris or for Entrapping Larger Particles A powder of spherical grains of polyvinylacetate (MW 500,000, Cat. No. 38, 793-2; Aldrich, Steinheim, G.) was separated by sieving. 40 mg of the finer particle fraction (100–200 μm) and 200 mg of the coarse fraction (200–500 μm) were layered into a QIAGEN spin column, provided with a plug at the outlet. After heating for one hr. at 130° C., and cooling for an additional hr., a filter element was obtained with the particles bound firmly to each other as well as to the polypropylene wall of the spin column. The capacity for entrapment was 8 mg of silica (LiChroprep Si 100, 25–40 μm, Cat. No. 1.13904.1000; Merck, Darmstadt, G.) when a suspension was filtered through the column.

EXAMPLE 20
Production of a Frit-syringe by Sintering Low-melting Thermoplastic Copolymer Containing Hydrophilic and Hydrophobic Chain Segments 50 mg of powdered poly (styrene-co-maleic acid) of MW 1,900 (Cat. No. 44, 235-6; Aldrich, Steinheim, G.) were pressed into the Luer orifice of a syringe provided with a caoutchouc stopper (Omnifix-F 1 ml; Braun; Melsungen, G.). After heating at 120° C. for two hrs followed by cooling for one hr., a frit-syringe was obtained. The resulting flow-rate of the frit-syringe thus produced was 3 ml/min at 100 mbar.

EXAMPLE 21
Preparation of a Polyfunctional Frit-syringe Using Polyacrylamide and Three Different Types of Adsorbent Particles A monomer solution was prepared at 50° C., using 4.5 g of acrylamide (Cat. No. A 3553; Sigma, Deisenhofen, G.), 0.5 g of N,N'-methylene-bis-acrylamide (Cat. No. M 7279; Sigma, Deisenhofen, G.) and 3.0 ml of dimethyl sulfoxide (Cat. No. D 8779; Sigma, Deisenhofen, G.). The monomer solution was used for suspending a mixture of 3 different types of microporous particles: 250 mg of anion exchanger based on silica gel (Adsorbex-SAX, Cat. No. 19845; Merck, Darmstadt, G.), 250 mg of cation exchanger (Adsorbex-SCX, Cat. No. 19846) and 250 mg of reversed-phase RP8 (Cat. No. 9362). Then, 250 μl of the suspension were applied into an 1 ml syringe (Omnifix-F; Braun, Melsungen, G.) provided with a microporous retaining tool. In addition, a top layer of degassed silicon oil (DC 200 fluid, 10 cst, Cat. No. 35132; Serva, Heidelberg, G.) was added which had been degassed meticuously under vacuum before. Finally, the piston of the syringe was inserted and pushed down to the compressed bed of particles. Polymerization was achieved by curing at 50° C. for 5 hrs. Finally, the filter-syringe was washed with several volumes of distilled water and upon drying, was washed further with several volumes of heptane.

EXAMPLE 22
Application of a Polyfunctional Frit-syringe for Fast Binding Studies with Ligands of Low Molecular Weight and, for Fast Removal of Dyes and Other Impurities A test solution was prepared containing per ml: 100 μg of bovine serum albumin together with $^{14}$C-labeled diluted tracer (NEN, Dreieich, G.). 3 μg of nile blue (Cat. No. 22,255-O; Sigma, Deisenhofen). 5 μg of methylorange (Cat. No. 11, 451-O; Sigma, Deisenhofen, G.) and 10 mM sodium phosphate buffer, pH 7.2. 50 μl of test solution were drawn into the frit-syringe prefilled with 400 μl of air and, were ejected within a 10 sec period. During this time, the dyes were found to be removed completely under complete recovery of protein in solution.

EXAMPLE 23
Production of Silica-containing Polymer Membranes Achieving Exclusion of Polymer from the Micropores of Microporous Particles by Means of Silicon Oil 1 gram of Ni-NTA Silica, 16–24 μm size (Cat. No. 30710; QIAGEN, Hilden, G.) was suspended with 9 ml of silicone oil (DC 200 fluid, 10 cst, Cat. No. 35132; Serva, Heidelberg, G.) by gentle stirring and sonification. 50 μl of the suspension were applied into a 100 μl-filtertip (Cat. No. 0030067.010; Eppendorf, Hamburg, G.) under controlled suction. When the fluid was flush with the top zone of the particle bed, a volume of 50 μl of a 10% solution of poly-(vinylalcohol-co-ethylene) (Cat. No. 41, 408-5; Aldrich, Deisenhofen, G.) in dimethyl sulfoxide was applied, followed by 50 μl of water. After drying, 300 μl of heptane were used for washing out traces of silicon oil.

EXAMPLE 24
Production of a Heat-stable, Solvent-resistant Epoxide Frit by Using a Sintered Polyvinyl-acetate Frit as a Temporary Channel-sparing Substance As described under example 19, a frit column was prepared using 20 mg of the finer particle fraction (100–200 μm) of polyvinyl acetate for sintering at 130° C. By pressure, a freshly mixed glue (UHU plus endfest 300, Cat. No. 45640; UHU GmbH Brühl, G.) was introduced avoiding inclusion of bubbles. Solidification was achieved upon reaction at 40° C. for one day. Finally, 0.5 mm of the lower end was cut off and the polyvinyl acetate was leached out using 100 ml of ethyl acetate under shaking for 24 hrs. The free inner volume of the frit was about 90% and the flow rate was 300 μl/sec.

EXAMPLE 25
Preparation of a Hydrophilic, Wettable Surface onto Polymer Surfaces by Applying a Polyol Ester Derivative of Poly(styrol-co-maleic acid)

A solution of 10% poly(styrene-co-maleic acid) (Cat. No. 44,235-6; Aldrich, Steinheim, G.) in dry dimethylformamide (Cat. No. 40258; Fluka, Buchs, CH) was prepared and supplemented with 0.3 volumes of dry glycerol (Cat. No. 49770; Fluka, Buchs, CH). To achieve esterification, the reaction mixture was held at 110° C. for 6 hrs, under exclusion of moisture. A coating solution was prepared by diluting 1 ml of product solution with 20 ml of dist water. Pipet tips were held dipped in the coating solution at ambient temperature overnight and were washed finally with twenty volumes of distilled water.

EXAMPLE 26
Production of a Membrane for Centrifugation Applications by Precipitation of a THF-solved Polymer by Contact with Ethanol Spin columns have been prepared by removing the filter membrane from a QIAshredder spin column (Cat. No. 79654; QIAGEN GmbH, Hilden, G). A solution of polystyrene (MW 800–5,000; Cat. No. 23637; Polysciences Inc., Eppelheim, G) in tetrahydrofurane (Cat. No. 87371; Fluka, Deisenhofen, G) was prepared by heating 5 g polystyrene with 45 g THF under reflux. 12 µl of this solution were pipetted in a spin column and the spin column dipped 5 mm deep into ethanol (Cat. No. 510; Bundesmonopolverwaltung für Branntwein, Düsseldorf, G). After 10 minutes 500 µl ethanol were pipetted on the column, and the column was removed from the ethanol bath. Positive pressure was applied on the column in order to press the nonsolvent through the column. The column was washed two times with ethanol and dried at room temperature. The flow rate of the thus obtained filter element with water was 100 µl/min (3.000 g in a Heraeus Biofuge 13).

EXAMPLE 27
Production of a Membrane for Gravity Flow Applications by Precipitation of a Toluene-solved Polymer by Contact with Ethanol 7.5 g polystyrene (MW 800–5,000; Cat. No. 23637; Polysciences Inc., Eppelheim G) in 42.5 g toluene (Cat. No. 89681; Fluka, Deisenhofen, G) were heated under reflux to prepare a 15% solution. 12 µl of this solution were pipetted in a spin column and the spin column dipped 5 mm deep into ethanol. After 10 minutes 500 µl ethanol were pipetted on the column, and the column was removed from the ethanol bath. Positive pressure was applied on the column in order to press the nonsolvent through the column for further precipitation of the polymer and removal of soluble components. The column was washed two times with ethanol and dried at room temperature. The flow rate of these columns was 100 µl/min (gravity flow).

EXAMPLE 28
Production of a Stable Membrane for High Centrifugation Speeds by Precipitation of a DMF-solved Polymer by Contact with Ethanol 5 g polystyrene (MW 800–5,000; Cat. No. 23637; Polysciences Inc., Eppelheim G) were heated with 45 g dimethyl formamide (Cat. No. 41644; Fluka, Deisenhofen, G) under reflux in order to obtain a homogeneous solution. 10 µl of this solution was applied on the outlet of a spin column. Then the spin column was dipped for 15 seconds 2 mm deep, then for 10 minutes 8 mm deep in an ethanol bath. The column was removed from the bath, and 500 µl of ethanol were applied to the column in order to complete the precipitation and to remove solvent. The column was treated with ethanol and positive pressure was applied as described in example 26. The thus obtained filter column was stable at centrifugations up to 10,000 g without destruction.

EXAMPLE 29
Production of a Membrane with Hydrophilic Properties by Precipitation of a DMSO-solved Polymer by Contact with Water 12 µl of a solution of 10% poly(methyl methacrylate) (MW 15,000, Cat No. 20,033-6; Aldrich, Steinheim, G) in dimethyl sulfoxide was applied to the inner surface of a spin column. The column was then dipped for 5 seconds 2 mm deep in a water bath, then dipped for 1 hour 10 mm deep into a water bath. After removing the column from the water bath, 500 µl water were pipetted on the column and allowed to flow slowly through the column. The column was washed two times with destined water to remove water-soluble contents and dried at 50° C. in an oven. The resulting flow rate of the thus produced porous column was 250 µl/min (gravity flow).

EXAMPLE 30
Production of a Mixed Membrane by Precipitation of a DMSO-solved Polymer Mixture by Contact with Water A volume of 12 µl of a 5% solution of poly-(vinylalcohol-co-ethylene), (Cat. No. 41,407-7; Aldrich, Steinheim, G) and 5% solution of poly(methyl methacrylate) in dimethyl sulfoxide was pipetted to the outlet of a spin column. Water was applied from the bottom of the polymeric solution by dipping the column 2 mm deep into water. After 10 seconds, the column was dipped 10 mm deep into water, and the membrane was allowed to harden for three hours. Then 500 µl of water were applied on the column for 30 minutes and the column was then removed from the water bath and put into a 2 ml collection tube (Cat. No. 19562; QIAGEN GmbH, Hilden, G). Water was allowed to flow through the membrane by centrifugation with 2,500 to 10,000 g in a centrifuge. After that, water was pipetted two more times and was forced through the membrane by centrifugation. The resulting flow rate was 250 µl/min (10,000 g in a Heraeus microcentrifuge).

EXAMPLE 31
Production of a Silica-containing Membrane by Precipitation of a DMSO-solved Polymer by Contact with Water for Means of DNA-binding 1 gram of LiChroprep Si 60, 15–25 µm size (Cat. No. 9336; Merck, Darmstadt, G) was mixed with 4 ml of a 5% polystyrene (MW 800–5.000) solution in dimethyl formamide, prepared by heating under reflux. 15 µl of the mixture was pipetted into the outlet of a spin column and the column dipped for 5 seconds 2 mm deep into water. After 10 seconds, the column was dipped 10 mm deep into water, and the membrane was allowed to harden for 2 hours. Then 500 µl of water were applied on the column for 10 minutes and the column was then removed from the water bath and put into a 2 ml collection tube. Water was allowed to flow through the membrane by centrifugation with 2,500 to 10,000 g. After that, water was pipetted two more times and was forced through the membrane by centrifugation. The filtration rate was 150 µl/min (11.000 g in a Heraeus microcentrifuge).

EXAMPLE 32
Production of a Ni-NTA Silica-containing Membrane by Precipitation of a DMF-solved Polymer by Contact with Water for Means of Protein Purification 1 gram of Ni-NTA Silica, 16–24 µm size (Cat. No. 30710; QIAGEN, Hilden, G) was mixed with 4 ml of a 10% polystyrene (MW 800–5.000) solution in dimethyl formamide by gentle stirring and sonification. 15 µl of the mixture were pipetted into the outlet of a spin column and the column dipped for 5 seconds 2 mm deep into water. After 10 seconds, the column was dipped for 60 minutes 10 mm deep into water. Then 500 µl of water were applied on the column for 5 minutes and the column was then removed from the water bath and put into a 2 ml collection tube. Water was allowed to flow through the membrane by centrifugation with 2,500 to 10,000 g. After that, water was pipetted two more times and was forced through the membrane by centrifugation. The filtration rate was 200 µ/min (11,000 g in a Heraeus microcentrifuge).

EXAMPLE 33
Production of a Silica-containing Two-layer Membrane by Precipitation of a DMF-solved Polymer by Contact with Water for Means of Filtration Two mixtures were prepared: 10 ml of a 5% solution of polystyrene (MW 800–5.000) in dimethyl formamide were mixed with 2 g LiChroprep Si 100, 25–40 μm size (Cat. No. 13904; Merck, Darmstadt, G) by vigorous stirring and sonification, and a second mixture was prepared by mixing 10 ml of a 5% solution of polystyrene (MW 800–5,000) in dimethyl formamide with 2 g LiChroprep Si 60, 40–63 μm size (Cat. No. 13905; Merck, Darmstadt, G). 12 μl of the first solution were pipetted to the outlet of a spin column and the spin column dipped for 10 seconds 1 mm deep under water. Then the spin column was removed from the water and 50 μl of the second solution were pipetted carefully on top of the first solution. The spin column was moved into the water bath and dipped 10 mm deep for 4 hours. After 500 μl of water were pipetted to the column, the column was put on a collection tube and water was forced through the membrane by centrifugation (2,500 to 10,000 g). Washing with water was repeated twice, and the membrane was dried by centrifugation at 13,000 g for 5 minutes.

EXAMPLE 34
Purification of Plasmid DNA by Chaotropic Binding on a Silica-containing Membrane (Example 31) and Elution by Lower Salt Concentration A solution of plasmid DNA in 10 mM Tris-buffer, pH 8.5, concentration 1 μg DNA/μl, was prepared by growing E. coli bacteria containing the plasmid pUC21 in a LB-Miller culture and separating the plasmid DNA from other cell components, following the QIAGEN plasmid mini purification protocol.

A slice of 200 mg agarose gel has been transferred into an Eppendorf tube, and 600 μl of a 4 M guanidine thiocyanate solution, pH 5.1, were added. The gel was completely dissolved in binding buffer by incubation at 50° C. for 10 minutes with occasional vortexing. After the gel slice has dissolved completely, 20 μl (20 μg) of the DNA solution were added, and the solution mixed in order to obtain a homogenous solution. Then 200 μl isopropanol were added, and the mixture was vortexed for five seconds. The spin column from example 31 was placed in a collection tube, and 750 μl of the thus prepared solution was pipetted on the column. After centrifugation at 13,000 g on a microcentrifuge, the column was loaded with the remaining solution, and was centrifuged again. Then 500 μl of the 4 M guanidine thiocyanate solution, pH 5.1, were added, and the spin column centrifuged again at 13,000 g for one minute, and the washing and centrifugation procedure was repeated with 750 μl 70% ethanol. Then the flow-through was discarded and the column centrifuged for an additional 1 minute at 13,000 rpm. The column was placed in a clean 1.5 ml microcentrifuge tube, and 100 μl of a 10 mM Tris-HCl solution, pH 8.5 were added on the column, and the DNA was eluted by centrifugation at full speed for one minute. For an increased elution, another 100 μl were added on the column, and the centrifugation was repeated.

The amount of DNA eluted from the column, quantified by spectroscopy and agarose gel, was 8–10 μg.

EXAMPLE 35
Isolation of a His-tagged Protein by Affinity Binding on a Ni-NTA Silica Containing Membrane (Example 32) and Elution with Lower pH A pQE vector, expressing 6× His tagged mouse dihydrofolatereductase (pQE 16, Cat. No. 33163; QIAGEN GmbH, Hilden, G), was transformed into E. coli strain M15 [pREP4], according to the protocol in The QIAexpressionist, March 1997, protein expression handbook; QIAGEN GmbH; 1997. Single colonies of transformants were picked into 1.5 ml culture medium containing 100 μg/ml ampicilin (Cat. No. 10045; Fluka, Deisenhofen, G) and 25 μg/ml kanamycin (Cat. No. 60615; Fluka, Deisenhofen, G) and grown at 37° C. overnight. 1 ml of the overnight culture was transferred into 100 ml culture of fresh medium, containing the above mentioned antibiotics. When the $OD_{600}$ measured by a photometer, reached 0.5 to 0.7, protein expression was induced by adding IPTG (Cat. No. 15502; Sigma, Deisenhofen, G) to a final concentration of 1 mM. The cells were allowed to grow an additional 4 hours and were then transferred to a microcentrifuge tube. Then centrifugation at 5,000 g for 10 minutes was started in order to harvest the cells as pellets. In the next step the cells were lysed in 10 ml denaturing lysis buffer (8 M urea (Cat. No. 51456; Fluka, Deisenhofen, G), 0.1 M $NaH_2PO_4$ (Cat. No. 71507; Fluka, Deisenhofen, G), 0.01 M Tris-HCl (Cat. No. 63362; Fluka, Deisenhofen, G), pH 8.0, by vortexing. The column from example 32 was equilibrated with denaturing lysis buffer, and then 400 μl of the thus produced protein solution (containing 200 μg 6× His-tagged mouse dihydrofolatereductase) were applied on the column. The column was placed in a 2 ml collection tube, the protein solution was allowed to flow through the column by centrifugation at 5,000 g, and the flow-through discarded. The spin column was washed by pipetting 600 μl of denaturing lysis buffer to the column, followed by centrifugation at 10,000 g for 2 minutes and discarding the flow-through. The washing procedure was repeated with denaturing washing buffer (8 M urea, 0.1 M $NaH_2PO_4$, 0.01 M Tris-HCl, pH 6.3). The spin column was placed in a 1.5 ml Eppendorf tube, and elution was carried out by pipetting 100 μl of denaturing elution buffer (8 M urea, 0.1 M $NaH_2PO_4$, 0.01 M Tris-HCl, pH 4.5), to the column, followed by centrifugation in a microcentrifuge at 5,000 g for 2 minutes. The elution was repeated two times, and the resulting protein concentration was measured according to Bradford's method. 20 μl of the single eluate fractions were mixed with 1 ml dye-solution (protein assay; Cat. No. 500-0006; Bio-Rad, München, G), allowed to incubate 5 minutes at room temperature, and measured with a Beckman photometer (wavelength 595 nm). The resulting total amount of protein, obtained from a spin column, was 40 μg.

EXAMPLE 36
Filtration of Bacterial Lysates by a Two-layer Membrane (Example 33) on a Vacuum Manifold A cell culture pellet was prepared by growing E. coli bacteria containing the plasmid pTZ19R in a LB-Miller culture and, after reaching an adsorption at 600 nm of 1–1.5, and centrifugation of 25 ml of the bacteria culture (3,000 rpm; Beckman centrifuge, Type J2-21, with inlet JA-17 for 50 ml falcon tubes) and removal of the supernatant. The thus obtained bacterial pellet was resuspended in 2.5 ml resuspension buffer (50 mM Tris-HCl, 10 mM EDTA, 100 μg/ml RNase A (Cat. No. 19101; QIAGEN GmbH, Hilden, G), pH 8.0), that no cell clumps remain unsuspended. The bacterial suspension was separated into 300 μl-portions by pipetting into 1.5 ml Eppendorf tubes. 300 μl lysis buffer (200 mM NaOH, 1% sodium dodecylsulfate (Cat. No. 71725; Fluka, Deisenhofen, G) were added and the solutions were mixed by gentle shaking of the tube. 300 μl of chilled neutralization buffer (3 M potassium acetate (Cat. No. 60035; Fluka, Deisenhofen, G), pH 5.5, were added, the solutions were mixed immediately, but gently, and the tube was chilled by incubation on ice for 10 minutes.

The two-layer membrane column (example 33) was placed on top of a luer adapter (Cat. No. 19541; QIAGEN GmbH, Hilden, G) on a QIAvac 6s vacuum chamber (Cat. No. 19503; QIAGEN, Hilden, G), and the lysate was pipetted to the column. When lower pressure (100 mbar) was applied, a clear filtrate without insoluble components was obtained, separated from cell debris. The DNA content of the filtrate was determined by an agarose gel.

EXAMPLE 37
Production of a Silica-containing Filter Membrane by Sintering a Mixture of Silica and Low-melting Polymer 10 mg of a mixture of Silica (LiChroprep Si 60, 5 μm size; Cat. No. 9336; Merck, Darmstadt, G) and polyvinyl acetate (MW 12,800, Cat. No. 43,043-9; Aldrich, Steinheim, G) was prepared and homogenized in a mortar with pestle. A spin column was closed by a plug. 30 mg of the mixture was filled into the closed spin column and the spin column was heated to 100° C. for two hours. Then the column was allowed to cool to room temperature and the plug was removed from the spin column.

The flow-rate was 100 μl/min (gravity flow).

EXAMPLE 38
Production of a Silica-containing Filter Membrane by Heating a Mixture of Silica and Polymer Solution A spin-column was closed with a plug and filled with 25 mg Silica (LiChroprep Si 60, 5 μm size; Cat. No. 9336; Merck, Darmstadt, G). A 20% solution of poly(methyl methacrylate) (Cat No. 20,033-6, Aldrich, Steinheim, G) in toluene was prepared by heating under reflux for 15 minutes. 60 μl of the solution were pipetted on the filled spin-column and the column heated to 100° C. for 3 hours. The flow rate of the thus obtained column was 150 μl/min (2,000 g in a Heraeus microcentrifuge).

EXAMPLE 39
Production of a Filter-strengthened Silica Membrane by Precipitation of a Polymer Solution on a Filter Device for Means of DNA-binding Under High Pressure Conditions Spin columns with membranes were prepared by removing Ni-NTA Silica powder from Ni-NTA Spin columns (Cat. No. 31016; QIAGEN GmbH, Hilden, G), and a mixture of 1 g LiChronrep Si 60, 15–25 μm size (Cat. No. 9336; Merck, Darmstadt, G) in 4 ml of a 5% solution of polystyrene (MW 800–5,000) was prepared as described in example 31. Then the column was put on a collection tube, 100 μl of water were pipetted to the membrane, and water was forced to flow through the membrane by centrifugation at 2,000 g for one minute. 75 μl of the polymer- and silica-containing mixture were pipetted on the column. The column was dipped for 1 hour 1 cm deep into water. 500 μl water were forced to flow through the column by appliance of high pressure. These column were stable against centrifugation up to 14,000 g, and the DNA capacity, measured as described in example 34, was 5 μg.

EXAMPLE 40
Production of a Filter-strengthened Silica Membrane by Precipitation of a Polymer Solution on a Filter Device for Means of Purification of Recombinant Proteins Under High Pressure Conditions Spin columns with membranes were prepared as described in example 14, and a mixture of 1 g Ni-NTA Silica, 16–24 μm size (Cat. No. 30710; QIAGEN GmbH, Hilden, G) in 4 ml of a 10% solution of polystyrene (MW 800–5,000) was prepared as described in example 32. Then the column was put on a collection tube, 100 μl of water were pipetted on the membrane, and water was forced to flow through the membrane by centrifugation at 2,000 g for one minute. 75 μl of the polymer- and Ni-NTA Silica-containing mixture were pipetted on the column, and the column was dipped for 1 hour 1 cm deep into water. 500 μl water were forced to flow through the column by appliance of high pressure. The thus obtained columns with Ni-NTA Silica are stable against centrifugation up to 14,000 g; the protein-binding capacity of these columns, detected as described in example 35, was 60 μg.

The present invention is not to be limited in scope by its specific embodiments described which are intended as single illustrations of individual aspects of the invention and any method, microporous and filter elements and uses thereof which are functionally equivalent are within the scope of the invention. Indeed, various modifications of the invention in addition to those shown and described therein will become apparent to those skilled in the art from the foregoing description and accompanying drawings. Said modifications intended to fall within the scope of the appended claims.

What is claimed is:

1. A method for producing a filter device comprising a support and a microporous element as a filter and/or absorption material, wherein the microporous element is generated within an aperture of the device by a process comprising the steps of:

(a) applying a substance present in a liquid phase wherein said liquid phase is a solution or suspension of one or more crosslinking monomers present in a solvent, said monomers further comprising a diamine and a polyepoxide, said substance further comprising solid porous or non-porous microparticles from 0.01 μm to 500 μm in size, wherein said microparticles contain an effector molecule capable of sequestering an ion, selectively binding to a solid support, binding to a preselected antigenic determinant or being a ligand, said effector molecule:

(i) comprises an enzyme or a remotely detectable moiety, or (ii) is capable of sequestering an ion and is selected from the group consisting of calmodulin, metallothionein, a fragment thereof, or an amino acid sequence rich in at least one of glutamic acid, aspartic acid, lysine, and arginine, or (iii) is capable of binding to a preselected antigenic determinant and is an antibody or fragment thereof, or (iv) is capable of selective binding to a solid support and is selected from the group consisting of GST, His-tag, or Lex-A, or (v) is a ligand and is Ni-NTA; and (b) causing solidification in spongy form of at least part of the substance wherein said solidification is caused by polymerizing said monomers.

2. The method according to claim 1, wherein the substance and the microparticles are present as a suspension in a non-solvent of low viscosity.

3. The method according to claim 2, wherein said substance and said microparticles are solidified by evaporating from a very diluted solution in a poor solvent or by sintering at moderate temperatures up to 130° C. without polymer solution, using only partially molten polymer instead.

4. The method according to claim 2 or 3, wherein said microparticles modify the adsorptive properties of the final microporous element, preferably useful for ion-exchange chromatography, adsorption chromatography at silica gels, reversed phase and/or hydrophobic interaction chromatography or affinity chromatography.

5. The method according to claim 1, wherein said effector molecule comprises an enzyme or remotely detectable moiety.

6. The method according to claim 1, wherein said effector molecule capable of sequestering an ion is calmodulin, metallothionein, a fragment thereof, or an amino acid sequence rich in at least one of glutamic acid, aspartic acid, lysine, and arginine.

7. The method according to claim 1, wherein said effector molecule capable of binding to a preselected antigenic determinant is an antibody or fragment thereof.

8. The method according to claim 1, wherein said effector molecule capable of selective binding to a solid support is GST, His-tag, or Lex-A.

9. The method according to claim 1, wherein said ligand is Ni-NTA.

10. A method for producing a filter device comprising a support and a microporous element as a filter and/or absorption material, wherein the support has the form of a tube, at least a section of said tube being conical in form, having a smaller and a larger cross-section end, and the microporous element is generated at or near to the smaller cross-section end of the conical section of said tube by a process comprising the steps of:

(a) applying a liquid substance wherein the substance is self-sustaining and applied to a support; and (b) causing solidification in spongy form of at least part of the substance.

11. The method according to claim 10, wherein the support is formed of polypropylene (PP), polyethylene (PE), propylene/ethylene copolymer, polyvinyl acetate, polyamide, polystyrene, polyethylene terephthalate (PET), polyether etherketon (PEEK), polycarbonate, polyethylene vinlyacetate, poly(vinyl alcohol-co-ethylene), polyester, polyamide, glass, ceramics quartz, silicon nitride, or mixtures thereof, or composite materials thereof with fibers or frames of glass, silicon dioxide, carbon, or ceramics.

12. The method according to claim 10, wherein the step of applying is accomplished by allowing the liquid substance to ascend in the tube by capillary action.

13. The method according to claim 10, wherein the inner wall of the tube is coated with a hydrophilic coating.

14. The method according to claim 13, wherein the edge of the tube next to the microporous element is kept free of hydrophilic coating.

15. The method according to claim 13, wherein the hydrophilic coating is formed by applying a solution of one or more polyvinyl esters or polyol derivatives of poly (styrene-co-maleic acid) in an organic solvent to the inner wall of the tube, allowing the organic solvent to evaporate.

16. The method according to claim 10, wherein the internal diameter of the tubular support is from 0.02 mm to 4 mm.

17. The method according to claim 10, wherein the substance is applied to a retainer.

18. The method according to claim 17, wherein the retainer is microporous.

19. The method according to claim 18, wherein the microporous retainer comprises solid particles connected with each other.

20. The method according to claim 18, wherein the microporous retainer is formed of polyethylene (PE), polypropylene (PP), propylene/ethylene copolymer, polyvinyl acetate, polyamide, polystyrene, polyethylene terephthalate (PET), polyether etherketon (PEEK), polycarbonate, poly(vinyl alcohol-co-ethylene), polyester, polyamide, glass, ceramics, quartz, silicon, silicon nitride, or mixtures thereof, stainless steel, or composite materials thereof with fibers or frames of glass, silicon dioxide, carbon, or ceramics.

21. The method according to claim 18, wherein the microporous retainer is in the form of a disc, grid, large-pore membrane, membrane with supporting fabric, membrane with woven or unwoven characteristics, net, plate, rod, or truncated cone.

22. The method according to claim 18, further comprising the step of arranging at least one microporous membrane at the microporous retainer.

23. The method according to claim 22, wherein the microporous membrane is formed of (regenerated) cellulose, polyamide, polyester, polypropylene (PP) or polytetrafluorethylene (PTFE).

24. The method according to any one of claims 17 to 23, wherein said retainer and/or said support is removed after solidification.

25. A filter device prepared according to the method of claim 1.

26. A filter device prepared according to the method of claim 18, wherein the polymer is attached to at least one part of the outer surface of the microporous retainer.

27. The filter device according to claim 26, wherein the microporous retainer contains in its pores the polymer in such a manner that the pores have residual free spaces forming channels allowing the flow of a fluid through the filter device.

28. The filter device according to claim 27, wherein the average diameter of the microparticles is less than 50% of the average diameter of the pores.

29. A kit comprising a filter device or filter element of any one of claims 25 to 28.

30. A filter device prepared according to the method of claim 10.

31. A kit comprising a filter device according to claim 30.

* * * * *

UNITED STATES PATENT AND TRADEMARK OFFICE
CERTIFICATE OF CORRECTION

PATENT NO. : 6,451,260 B1  
DATED : September 17, 2002  
INVENTOR(S) : Andreas Dusterhoft, Thomas Manz, Ehrenfried Mehl and Friedrich Lollspeich It is certified that error appears in the above-identified patent and that said Letters Patent is hereby corrected as shown below:

<u>Title page,</u>
Item [73], correct the named Assignee to read:
-- [73]   Assignee:  Qiagen GmbH, Hilden (DE); and Max-Planck-Gesellschaft zur Förderung der Wissenschaften e.V., Berlin (DE) --

Signed and Sealed this

Tenth Day of December, 2002

JAMES E. ROGAN
*Director of the United States Patent and Trademark Office*